(12) United States Patent
Kok-Jacon et al.

(10) Patent No.: US 8,269,064 B2
(45) Date of Patent: Sep. 18, 2012

(54) TRANSFORMED PLANT EXPRESSING A MUTANSUCRASE AND SYNTHESIZING A MODIFIED STARCH

(75) Inventors: Geraldine Kok-Jacon, Hamme-Mille (BE); Jean-Paul Vincken, Renkum (NL); Luc C J M Suurs, Zetten (NL); Claus Frohberg, Kleinmachnow (DE); Richard G F Visser, Bennekom (NL)

(73) Assignee: Bayer CropScience AG, Monheim (DE)

( * ) Notice: Subject to any disclaimer, the term of this patent is extended or adjusted under 35 U.S.C. 154(b) by 703 days.

(21) Appl. No.: 11/794,610

(22) PCT Filed: Jan. 9, 2006

(86) PCT No.: PCT/EP2006/000232
§ 371 (c)(1),
(2), (4) Date: May 18, 2009

(87) PCT Pub. No.: WO2006/072603
PCT Pub. Date: Jul. 13, 2006

(65) Prior Publication Data
US 2009/0300798 A1    Dec. 3, 2009

Related U.S. Application Data

(60) Provisional application No. 60/643,125, filed on Jan. 11, 2005.

(30) Foreign Application Priority Data

Jan. 10, 2005   (EP) .................................. 05356008

(51) Int. Cl.
*A01H 5/00* (2006.01)
*C12P 19/04* (2006.01)
*C12N 15/82* (2006.01)

(52) U.S. Cl. ........ 800/284; 800/298; 435/101; 435/468; 435/419

(58) Field of Classification Search .................... 800/284
See application file for complete search history.

(56) References Cited

U.S. PATENT DOCUMENTS 6,794,558 B1    9/2004   Frohberg

FOREIGN PATENT DOCUMENTS

| CN | 1316003 A | | 10/2001 |
| JP | 2000316571 | * | 5/1999 |
| WO | WO 95/13389 | | 5/1995 |
| WO | WO 00/08175 | | 2/2000 |
| WO | WO 00/47727 | * | 8/2000 |

OTHER PUBLICATIONS

Kok-Jacon et al., Mutan Produced in Potato Amyloplast Adheres to Starch Granules, 2005, Plant Biotechnology Journal, vol. 3, pp. 341-351.*
Monchois et al, FEMS Microbiology Reviews 23 (1999) 131-151.*
Kok-Jacon (Research Projects 2002, Laboratory of Plant Breeding—Available online 2002).*
Anonymous "Research Projects 2002, Laboratory of Plant Breeding, Wageningen University and Research Centre." Retrieved from the internet on Nov. 5, 2005.
Gerrits, et al. (Feb. 2001) "Sucrose metabolism in plastids." Plant Physiology 12592): 926-934.
Ji, et al. (Mar. 2003) "Microbial starch-binding domains as a tool for targeting proteins to granules during starch biosynthesis." Plant Molecular Biology 51(5): 789-801.
Kok-Jacon, et al. (Jul. 2003) "Towards a more Versatile Alpha-Glucan Biosynthesis in Plants." Journal of Plant Physiology 160(7): 765-777.
Kok-Jacon, et al. (2005) Plant Biotechnology Journal 3(3): 341-351.
Oakes, et al. (1991) Biotechnology 9: 982-986.
Quirasco, et al. (1999) Applied Environmental Microbiology 65(12): 5504-5509.
Monchois, Vincent et al., "Glucansucrases: mechanism of action and structure-function relationships," FEMS Microbiology Reviews, vol. 23, pp. 131-151, 1999.
Shimamura, Atsunari et al., "Identification of Amino Acid Residues in *Streptococcus mutans* Glucosyltransferases Influencing the Structure of the Glucan Product," Journal of Bacteriology, vol. 176, No. 16, pp. 4845-4850, Aug. 1994.

* cited by examiner

*Primary Examiner* — Anne Marie Grunberg
*Assistant Examiner* — Lee A Visone
(74) *Attorney, Agent, or Firm* — Hunton & Williams LLP

(57) ABSTRACT

The present invention relates to plant cells and plants, which are genetically modified, wherein the genetic modification leads to the expression in plastids of such plant cells and plants of an enzyme having the activity of a mutansucrase. Furthermore, the present invention relates to means and methods for the manufacture of such plant cells and plants. Plant cells and plants of this type synthesise a modified starch. The present invention therefore also relates to the starch synthesised by the plant cells and plants according to the invention as well as to methods for the manufacture of the starch and to the manufacture of starch derivatives of this modified starch.

24 Claims, 3 Drawing Sheets

TRANSFORMED PLANT EXPRESSING A MUTANSUCRASE AND SYNTHESIZING A MODIFIED STARCH

CROSS-REFERENCE TO RELATED APPLICATIONS

This application is the national stage filing of PCT/EP2006/000232, filed Jan. 9, 2006, which claims priority to EP 053 56 008.2, filed Jan. 10, 2005, and U.S. Provisional Patent Application No. 60/643,125, filed Jan. 11, 2005, the disclosures of each of which is hereby incorporated by reference.

BACKGROUND OF THE INVENTION (i) Field of the Invention:

The present invention relates to plant cells and plants, which are genetically modified, wherein the genetic modification leads to the expression in plastids of such plant cells and plants of an enzyme having the activity of a mutansucrase. Furthermore, the present invention relates to means and methods for the manufacture of such plant cells and plants. Plant cells and plants of this type synthesise a modified starch. The present invention therefore also relates to the starch synthesised by the plant cells and plants according to the invention as well as to methods for the manufacture of the starch and to the manufacture of starch derivatives of this modified starch.

(ii) Description of the Related Art:

With respect to the increasing significance which has recently been ascribed to vegetal substances as regenerative sources of raw materials, one of the objects of biotechnological research is to try to adapt vegetal raw materials to the demands of the processing industry. In order to enable the use of regenerative raw materials in as many areas as possible, it is furthermore important to obtain a large variety of substances. Apart from oils, fats and proteins, polysaccharides constitute the essential regenerative raw materials derived from plants. Apart from cellulose, starch maintains an important position among the polysaccharides, being one of the most significant storage substances in higher plants.

Starch is deposited as granules in the chloroplasts of green leaves (transitory starch) and in amyloplasts of tubers, roots and seeds (storage starch) (Kossmann and Lloyd 2000).

The polysaccharide starch is a polymer made up of chemically homogeneous basic components, namely the glucose molecules.

However, it constitutes a highly complex mixture from various types of molecules which differ from each other in their degree of polymerization and in the degree of branching of the glucose chains. Therefore, starch is not a homogeneous raw material. One differentiates particularly between amylose-starch, a basically non-branched polymer made up of alpha-1,4-glycosidically branched glucose molecules, and amylopectin-starch which in turn is a complex mixture of various branched glucose chains. The branching results from additional alpha-1,6-glycosidic interlinkings.

In plant storage organs, starch biosynthesis takes place within the amyloplast and is the result of different reactions such as synthesis (polymerization of glucosyl residues), rearrangement and degradation, in which various starch synthases (E.C.2.4.1.21), transferases (branching (E.C.2.4.1.18) and disproportionating enzyme (E.C.2.4.1.25)), and is hydrolytic enzymes (debranching enzyme (E.C.3.2.1.41)), respectively, play key roles.

In order to enable as wide a use of starch as possible, it seems to be desirable that plants be provided which are capable of synthesizing modified starch which is particularly suitable for various uses. One possibility to provide such plants—apart from breeding methods—is the specific genetic modification of the starch metabolism of starch-producing plants by means of recombinant DNA techniques.

Over the years, several studies have been done aimed at turning the amyloplast into a more versatile polysaccharide factory. For this purpose, several microbial enzymes have been equipped with a plastidial targeting transit, and their influence on starch structure and functionality has been investigated.

Certain bacteria possess an array of enzymes, so-called glucansucrases, which can attach (contiguous) 1,6-linked or 1,3-linked glucosyl residues to maltodextrins. With few exceptions, glucansucrases are extracellular enzymes, which are produced by lactic acid bacteria such as *Leuconostoc mesenteroides* strains, oral Streptococci, and some species of *Lactobacillus* and *Lactococcus* (Robyt 1995; van Geel-Schutten et al. 1999). In addition, they are produced by other bacteria such as some of the *Neisseria* strains (Hehre et al. 1949). These strains are involved in different processes in nature. Some of the strains colonize the oral cavity of humans and animals and can induce the formation of dental caries. Other strains can invade the throat such as the commensal *Neisseria* species. Some *Lactobacillus* species increase the viscosity of fermented milk (de Vuyst and Degeest 1999).

The glucansucrases catalyse the polymerisation of glucose residues from sucrose, which leads to the production of a large variety of α-glucans with different sizes and structures, and composed of diverse linkage types.

The elongation of glucan chains by glucansucrases is quite different compared to that by starch synthases. First, the preferred substrate is sucrose instead of ADP-Glucose. Second, the glucose residues are added to the reducing end of a growing glucan chain by a so-called two-site insertion mechanism (Robyt 1995).

In addition, the branching of glucans does not take place by means of a branching enzyme as in starch biosynthesis, but by a so-called acceptor reaction catalyzed by the glucansucrases themselves (Robyt, 1995). The glucansucrase is thought to contain an acceptor-binding site that can bind acceptor molecules such as the nascent glucan chains or maltodextrins (Su and Robyt, 1994). The efficiency to catalyse acceptor reactions, particularly with starch polymers. or maltodextrins is nevertheless unpredictable, as the structure-function relationships underlying the acceptor reaction are not understood and is poorly documented. It seems nevertheless that the relative acceptor efficiency depends on the size of the acceptor molecules (Fu et al. 1990), and it is uncertain that amylopectine and amylose may be acceptor molecules for glucansucrases.

Glucansucrases can be classified according to the structure of the glucan formed, and in particular the nature and frequency of the glucosidic linkages synthesized.

Expression of the GTFI (EC 2.4.1.5) mutansucrase enzyme (Ferretti et al., 1987), which is produced by the oral cariogenic *Streptococcus downei* MFe28 bacteria leads to the accumulation of glucan polymers, called mutans, in presence of sucrose. Mutan polymers are composed of mainly α-(1→3) glucosidic bonds with few α-(1→6) branch point. Due to their high proportion of α-(1→3)-linked glucose residues in the main chain (88%), mutan polymers are water-insoluble, while α-(1→6)-linked glucose residues in the side chains (12%) contribute to their adhesive properties.

Mutan polymers count for about 70% of the carbohydrates present in dental plaque (Loesche, 1986) resulting in the action of various bacterial agents. Briefly, saliva-coated enamel surfaces are colonized by diverse oral bacteria, referred to as the early colonizers, that adhere to receptors present on teeth surfaces by means of adhesins proteins. In turn, these bacteria secrete various polysaccharides such as mutans, dextrans and levans that exhibit different degrees of water-solubility (Sutherland, 2001). These polymers together with the early colonizers enhance the aggregation of the late colonizers creating a biofilm, which is usually named dental plaque (Marsh, 2003). From the polymers that are formed, mutan is the most adhesive and water-insoluble polymer.

Due to their implications in human dental caries, different studies based on genetic engineering of GTFI have been carried out in order to elucidate its structure-function relationship. Interestingly, expression of only its catalytic domain resulted in an active GTFI enzyme, for about 70% (Monchois et al., 1999b).

The nucleic acids sequence of the gene gtfI from *Streptococcus downei* Mfe28 bacteria has been reported in Ferreti et al, 1987, J. of Bacteriology, p 4271-4278.

Starch polymer modification has been achieved by targeting the *Escherichia coli* glycogen synthase (GLGA) and the glycogen branching enzyme (GLGB) to the potato amyloplast (Shewmaker et al. 1994; Kortstee et al. 1996). In both cases, the natural balance of chain elongation and branching was disturbed, resulting in starch granules with altered physical properties, and with more heavily branched polymers.

Attachment of novel glycosyl residues to starch polymers has also been an objective. For this purpose, a *Bacillus subtilis* levansucrase (E.C.2.4.1.10) was introduced in potato tuber amyloplasts (Gerrits et al. 2001). Levansucrase can polymerize the fructose moiety of the donor substrate sucrose into a high molecular weight fructan. Nevertheless, the starch yield was severely compromised and the starch morphology was dramatically altered.

It has also been tried to convert starch in planta into high-value cyclic oligosaccharides, which can accommodate hydrophobic substances in their apolar cavity and can be used in various food and pharmaceutical applications. A cyclodextrin glycosyltransferase (CGTase; E.C.2.4.1.19) from *Klebsiella pneumoniae* was introduced into potato amyloplasts (Oakes et al. 1991) for cyclodextrin production. Only 0.01% of the endogenous starch was converted to the desired product, and this product was difficult to recover from the plant material.

These examples demonstrate that bacterial enzymes can be potentially powerful tools for starch modification, but that their performance in the plant is unpredictable beforehand (Kok-Jacob A. et al, 2003).

SUMMARY OF THE INVENTION

The object of the present invention is therefore based on providing modified starch, new plant cells and/or plants, which synthesise such a modified starch, as well as methods for producing said plants.

DETAILED DESCRIPTION OF THE INVENTION

Figure 1:
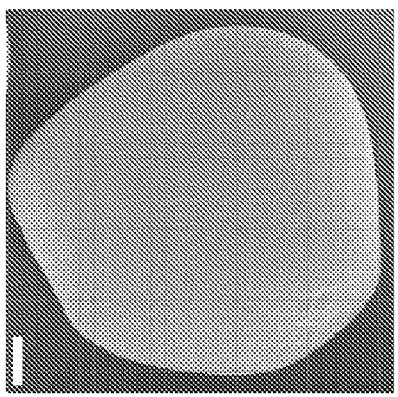
FIG. 1: Modified starch granules observed by scanning electron microscopy analysis performed on the starch of selected potato plants transformed with the mature mutansucrase gene (J-K) or with a truncated mutansucrase gene (L-M), compared to the starch of a wild type Kardal plant (I).
Figure 1:
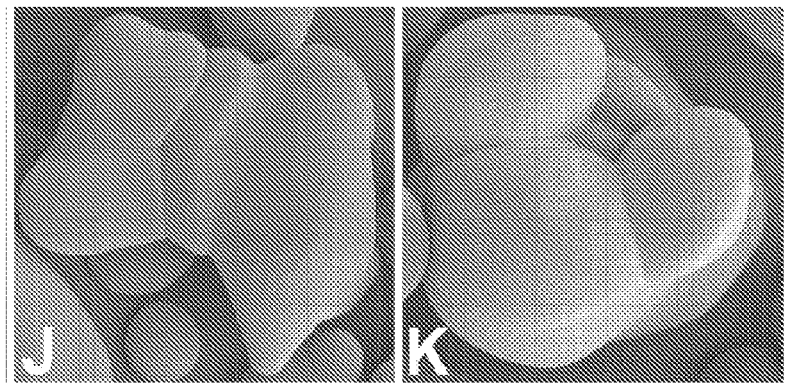
Figure 1:
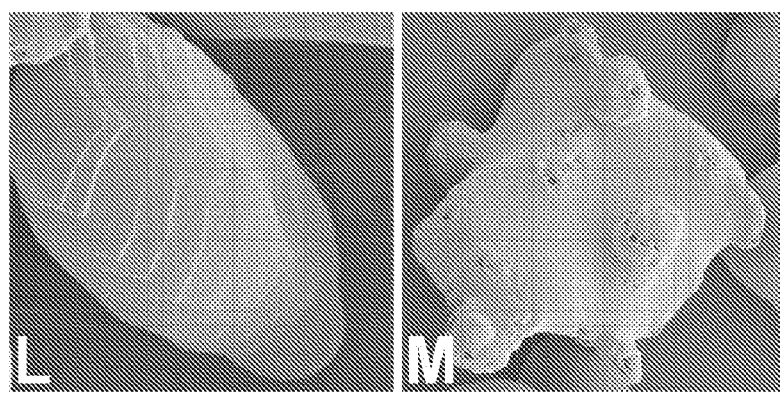

Therefore, the present invention relates to genetically modified plant cells or genetically modified plants characterized in that they show an enzymatic activity of a mutansucrase protein in plastids and wherein said genetically modified plant cells or genetically modified plants synthesize a modified starch in comparison to starch synthesized by corresponding non-genetically modified wild-type plant cells or wild type plants, respectively.

The term "genetically modified" or "transformed" refers to a plant cell or a plant having stably integrated in its genome at least one transgene. Preferentially, the transgene comprises a chimeric nucleic acid sequence comprising at least one element originating from another organism than the transformed plant cell or transformed plant (heterologous transgene). Particularly, the transgene is a recombinant transgene which comprises at least a promoter, a coding sequence and optionally a termination signal. More preferably the coding sequence of the recombinant transgene encodes a mutansucrase protein, most preferably a mutansucrase GTFI protein.

In conjunction with the present invention, the term "wild type plant cell" or "wild type plant" means that the plant cells or plants concerned were used as starting material for the manufacture of the plant cells according to the invention, i.e. their genetic information, apart from the introduced genetic modification, corresponds to that of a plant cell according to the invention.

In conjunction with the present invention, the term "corresponding" means that, in the comparison of several objects, the objects concerned that are compared with one another have been kept under the same conditions. In conjunction with the present invention, the term "corresponding" in conjunction with "wild type plant cell" or "wild type plant" means that the plant cells or plants, which are compared. with one another, have been raised under the same cultivation conditions and that they have the same cultivation age.

Here, within the framework of the present invention, the term "activity" means the expression of a transgene coding sequence and/or the presence of the protein encoded by a transgene coding sequence and/or the presence of the product produced by the protein encoded by the transgene in the genetically modified plant cells or genetically modified plants, respectively.

The expression of a coding sequence of a transgene can, for example, be determined by measuring the quantity of transcripts of the transgene, e.g. using Northern blot analysis or RT-PCR.

The presence of a protein encoded by a transgene, which results in an activity of the respective protein in the genetically modified plant cells or genetically modified plants concerned, can, for example, be determined by immunological methods such as Western blot analysis, ELISA (Enzyme Linked Immuno Sorbent Assay) or RIA (Radio Immune Assay). In case the transgene encodes a mutansucrase protein, the presence of the protein in genetically modified plant cells or genetically modified plants can be demonstrated, for example, with the help of native acrylamide gel electrophoresis. In doing so, plant cell or plant extracts containing proteins are first separated electrophoretically and, after incubation of the acrylamide gels in respective buffers containing sucrose, the acrylamide gels show a white precipitate at the location of the mutansucrase protein. Additionally the mutan produced by the mutansucrase protein in the gel can be stained with an erythrosine red colouring agent (according to method 6 in general methods).

The presence of the product mutan produced in plant cells according to the invention or plants according to 'the invention' having been transformed with a nucleic acid sequence encoding a mutansucrase protein can be demonstrated e.g. by immunological. analysis. A further method for the detection of mutan present in plant cells is the staining with an erythrosine red colouring agent (according to method 5 in general methods).

In conjunction with the present invention, the term "mutansucrase protein" is to be understood as an enzyme capable of catalysing the synthesis of mutan from sucrose, wherein the mutan comprises predominatly alpha-1,3-linked glucose units.

Preferably the amount of alpha-1,3-linkages in the mutan produced by a mutansucrase protein is at least 75%, more preferably at least 80%, especially preferably at least 85% and most preferably at least 88%.

The term "mutansucrase protein" is further defined as an enzyme having an identity of at least 70%, preferably at least 80%, more preferably at least 90%, and still more preferably at least 95% with the amino acid sequence identified under SEQ ID NO: 2 or parts thereof having the capability of catalysing the synthesis of mutan from sucrose.

Most glucansucrases, including mutansucrase proteins, share a common structure composed of four different regions: a signal peptide, a variable region, a catalytic domain, and a C-terminal (glucan-binding) domain (GBD). (Monchois et al., 1999, FEMS Microbiology Letters 177, 243-248; Monchois et al., 1999, FEMS Microbiology Reviews 23, 131-151).

The signal peptide consists of 35-38 amino acids and is responsible for secretion of the sucrases, when expressed by their natural bacterial hosts. The signal peptide is followed by a variable region of 140-261 amino acids.

The catalytic domain or active core region is composed of about 900 amino acids and is highly conserved within the *Leuconostoc* and *Streptococcus* species (MacGregor et al. 1996). The catalytic domain is also called the sucrose-binding domain because it contains a catalytic triad of aspartic and glutamic acid residues that play an important role in binding and cleavage of sucrose molecules. Mutansucrase proteins with various mutations in single amino acids which are part of the catalytic domain have been analysed in respect with the influence of the respective mutation on the structure of the glucan produced and the catalytic activity of the respective mutansucrase protein (Shimamura et al., 1994, J. Bacteriology 176(16), 4845-4849).

The glucan-binding domain is covering about 500 amino acids, and is composed of repeats named A, B, C, D that are defined by a consensus sequence (Monchois et al 1998, 1999). Nevertheless, the number and organization of these repeats is variable within glucansucrases, and it has been shown that the minimum number of these repeated units necessary to ensure glucan binding properties is different according to the enzymes, and more particularly is different for enzymes producing a soluble glucan than for those producing an insoluble one (Monchois et al., 1999).

However, it is well known by a person skilled in the art, that a mutansucrase protein capable to synthesize mutan can be a protein comprising the entire amino acid sequence of the corresponding naturally occurring protein (full length mutansucrase protein) or a variant thereof. Variants of mutansucrase proteins can be proteins comprising only the amino acids of the mature, naturally occurring mutansucrase protein, lacking the amino acids encoding naturally occurring signal sequences, like e.g. signal sequences leading. to the secretion of a bacterial mutansucrase protein to the culture medium. Further variants of mutansucrase proteins comprise fragments, derivatives and allelic variants of naturally occurring mutansucrase proteins which encode a catalytically active mutansucrase protein (catalytically active truncated mutansucrase protein).

Examples of catalytically active truncated enzymes are reported in Monchois et al, 1999. In particular, the signal peptide and N-terminal highly variable region are not required to have fully catalytically active mutansucrase proteins. Catalytically active truncated mutansucrase proteins encoded by engineered gtfi genes encoding only the conserved catalytic domain (active core region), or the active core region with either full-length or truncated C-terminal domains, are active enzymes capable of catalysing the synthesis of mutan from sucrose (Monchois et al, 1999).

It has been surprisingly found that genetically modified plant cells or genetically modified plants showing an enzymatic activity of a catalytically active truncated mutansucrase. protein in plastids synthesize a starch which is further modified in comparison to modified starch synthesized by genetically modified plant cells or genetically modified plants, respectively, which show an enzymatic activity of a mature mutansucrase protein in plastids.

Therefore further objects of the invention are genetically modified plant cells or genetically modified plants characterized in that they show an enzymatic activity of a catalytically active truncated mutansucrase protein in plastids and wherein said genetically modified plant cells or genetically modified plants synthesize a modified starch in comparison to starch synthesized by corresponding non-genetically modified wild-type plant cells or corresponding non-genetically modified wild type plants, respectively.

In conjunction with the invention the term "catalytically active truncated mutansucrase protein" is defined as an enzyme comprising at least the amino acids of the active core region of a naturally occurring mutansucrase protein.

A catalytically active truncated mutansucrase protein therefore can comprise only the amino acid sequences encoding the active core region or can comprise amino acid sequences encoding the active core region and in addition amino acid sequences selected from the group consisting of a) amino acid sequences constituting a full length or truncated variable region,
b) amino acid sequences constituting a full length or truncated C-terminal domain,
c) amino acid sequences constituting a truncated C-terminal domain and amino acid sequences constituting a full length variable region.
d) amino acid sequences constituting a full length C-terminal domain and amino acid sequences constituting a truncated variable region.
e) amino acid sequences constituting. a truncated C-terminal domain and amino acid sequences constituting a truncated variable region.

Preferred catalytically active truncated mutansucrase proteins are mutansucrase proteins where the entire amino acid sequences encoding the C-terminal domain has been deleted.

Thus, these catalytically active mutansucrase proteins comprise amino acid sequences encoding the active core region and in addition. amino acid sequences encoding the variable region.

Another preferred catalytically active mutansucrase protein comprises the amino acid sequence of the active core region and parts of the variable region.

In conjunction with the invention the term "active core region" is further defined as a protein comprising at least an amino acid sequence having an identity of at least 70%, preferably at least 80%, more preferably at least 90%, and still more preferably at least 95% with the amino acid sequence of the core region identified under SEQ ID NO: 4 from position 109 to 1012.

A preferred catalytically active mutansucrase protein comprises an amino acid sequence having an identity of at least 70%, preferably at least 80%, more preferably at least 90%, and especially preferably at least 95% with the amino acid sequence as identified under SEQ ID NO. 4.

In conjunction with the present invention, the term "transgene" is understood to mean such a molecule that either does not occur naturally in the corresponding non-genetically modified wild type plant cells or non-genetically modified wildtype plants, or that does not occur naturally in the concrete spatial arrangement in non-genetically modified wild type plant cells or non-genetically modified wildtype plants, or that is localised at a place in the genome of the non-genetically modified wild type plant cell or non-genetically modified wildtype plant at which it does not occur naturally.

In conjunction with the invention the term "recombinant" means a nucleic acid molecule which consists of different elements, the combination or specific spatial arrangement of which does not occur naturally in plant cells or plants.

A large number of techniques are available for the introduction of DNA into a plant host cell. These techniques include the transformation of plant cells with T-DNA using *Agrobacterium tumefaciens* or *Agrobacterium rhizogenes* as the transformation medium, the fusion of protoplasts, injection, the electoporation of DNA, the introduction of DNA by means of the biolistic approach as well as other possibilities.

The use of agrobacteria-mediated transformation of plant cells has been intensively investigated and adequately described in EP 120516; Hoekema, IN: The Binary Plant Vector System Offsetdrukkerij Kanters B. V., Alblasserdam (1985), Chapter V; Fraley et al., Crit. Rev. Plant Sci. 4, 1-46 and by An et al. EMBO J. 4, (1985), 277-287. For the transformation of potato, see Rocha-Sosa et al., EMBO J. 8, (1989), 29-33, for example.

The transformation of monocotyledonous plants by means of vectors based on *agrobacterium* transformation has also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et. al., Bio/Technology 13, (1995), 486-492; Conner and Domisse, Int. J. Plant Sci. 153 (1992), 550-555; Ritchie et al, Transgenic Res. 2, (1993), 252-265). An alternative system to the transformation of monocotyledonous plants is transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, electroporation of partially permeabilised cells and the introduction of DNA by means of glass fibres. In particular, the transformation of maize has been described in the literature many times (cf. e.g. WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726).

The successful transformation of other types of cereal has also already been described, for example for barley (Wan and Lemaux, see above; Ritala et al., see above; Krens et al., Nature 296, (1982), 72-74) and for wheat (Nehra et al., Plant J. 5, (1994), 285-297). All the above methods are suitable within the framework of the present invention.

In conjunction with the present invention, the introduced nucleic acid may be integrated into the nuclear genome or into the plastidial genome of the plant cell.

The classical way of transfecting plastids involves bombarding leaves with microprojectiles carrying DNA molecules (Svab et al., 1993). Today, stable plastid transfection is routinely performed in the tobacco species *N. tabaccum* (Svab and Maliga, 1990; Svab et al., 1993). There has been recent progress in rice (Khan and Maliga, 1999), *Arabidopsis thaliana* (Sikdar et al., 1998), potato (Sidorov et al., 1999), colza (WO 00/39313), tomato (Ruf et al., 2001) and soybean (WO 04/053133). Examples of methods for obtaining transplastomic plants have been described in Patent Application WO 04/055191.

Amongst other things, the plant cells according to the invention and the plants according to the invention can be differentiated from wild type plant cells and wild type plants respectively in that they contain at least one copy of a foreign nucleic acid molecule (transgene) stably integrated within their genome, wherein the foreign nucleic acid molecule encodes a mutansucrase protein or a catalytically active truncated mutansucrase protein.

Furthermore, the plant cells according to the invention and the plants according to the invention can preferably be differentiated from wild type plant cells or wild type plants respectively by the following characteristic: the plant cells according to the invention or plants according to the invention have transcripts of the introduced nucleic acid molecules. These can be verified, for example, by Northern blot analysis or by RT-PCR (Reverse Transcription Polymerase Chain Reaction). Preferably, the plant cells according to the invention and the plants according to the invention contain a protein, which is coded by an introduced nucleic acid molecule. This can be demonstrated by immunological methods, for example, in particular by a Western Blot Analysis.

Furthermore the plant cells according to the invention and the plants according to the invention can more preferably be differentiated from wild type plant cells or wild type plants, respectively, by the characteristics that they synthesize mutan. Preferably the plant cells of the invention or the plants of the invention produce mutan in their plastids.

The terms "starch which is modified in comparison to starch synthesized by wild-type plant cells" or "modified starch" or "altered starch" mean a starch which, when compared to starch synthesized in wild-type plants, differs for example in its physico-chemical properties, the pastification behavior, the size and/or the shape of the starch granule. Compared with wild-type starch, such starch may be modified in particular with respect to its viscosity and/or the gel formation properties of the glues of this starch and/or an increased gel stability and/or its capability to be digested and/or the granule morphology.

The modification in respect to the viscosity can be measured by several means, and in particular by means of a Thermo Haake rheoscope (Thermo Electron Cooperation) according to the manufacturer's instructions or by means of a Rapid Visco Analyser (RVA), as for example the Rapid Visco Analyser Super3 (Newport Scientific Pty Ltd, Investmet Support Group, Warriewod NSW 2102, Australia). The viscosity values are indicated in Centipoise (cP) in accordance with the manufacturer's operating manuals, which are incorporated into the description herewith by reference.

A preferred way to determine the viscosity characteristics by means of a Rapid Visco Analyser (RVA) and the parameters which are used for the comparison of different samples are described in the general methods (method 1) of the present invention.

Another preferred way to determine the viscometric profiles by means of a thermo Haake rheoscope is described in the general methods (method 2) of the present invention.

The determination of the gel formation properties of the glues of the starch (or gel strength) and/or the gel stability can be determined by means of a Texture Analyser, as for example the Texture Analyser TA-XT2 (Stable Micro Systems—Surrey, UK) in accordance with the manufacturer's operating manual, which is incorporated into the description herewith by reference.

A preferred way to determine the gel formation properties of the glues of the starch by means of the Texture Analyser TA-XT2 is described in the general methods (method 3) of the present invention.

The capability to be digested can be determined by the determination of the percentage of digested starch, using the methodology of Englyst H.N. et al., European Journal of Clinical Nutrition 4, Suppl. 2, S33-S50, which is incorporated into the description herewith by reference, based on the determination of resistant starches RS Type III, which is the indigestible retrograded starch that is obtained, for example, by thermal and/or enzymatic treatment and then retrograded.

The method of Englyst can be modified in correspondence with the information on the determination of RS content in WO 00/02926, incorporated into the description herewith by reference. The resulting method is described in the general methods (method 4) of the present invention.

Further, the present invention relates to genetically modified plant cells or genetically modified plants of the invention characterized in that said plant cells or said plants, respectively, synthesize a modified starch which has an increased T-onset temperature, and/or an increased minimum viscosity, and/or an increased end viscosity, and/or an altered granule morphology, in comparison to starch synthesized by wild-type plant cells.

In conjunction with the invention, the T-onset temperature, minimum viscosity and end viscosity can be measured by means of a rheoscope, particularly a Thermo Haake rheoscope or a Rapid Visco Analyser. Preferred methods are described in general methods (methods 1 and 2) of the present invention.

Genetically modified plant cells or genetically modified plants characterized in that they show an enzymatic activity of a catalytically active truncated mutansucrase protein in their plastids and wherein said genetically modified plant cells or genetically modified plants synthesize a starch which has an increased T-onset temperature. and/or an altered granule morphology and/or an increased minimum viscosity and/or an increased end viscosity in comparison to starch synthesized by corresponding non-genetically modified wild-type plant cells or corresponding non-genetically modified wild-type plants, respectively, are further objects of the invention.

Preferably, the increase of the T-onset temperature is at least of 0.5% when genetically modified plant cells or genetically plants show an enzymatic activity of a mature mutansucrase, and at least of 0.5%, preferred at least, of 1%, more preferred at least of 1.5%, most preferred at least of 2% when genetically modified plant cells or genetically plants show an enzymatic activity of a catalytically active truncated mutansucrase protein.

Preferably, the increase of the minimum viscosity is at least of 5%, preferred at least of 10% when genetically modified plant cells or genetically plants show an enzymatic activity of a mature mutansucrase, and at least of 10%, preferred at least of 40%, more preferred at least of 70%, most preferred at least of 100% when genetically modified plant cells or genetically plants show an enzymatic activity of a catalytically active truncated mutansucrase protein.

Preferably, the increase of the end viscosity is at least of 1.5%, preferred at least of 3% when genetically modified plant cells or genetically plants show an enzymatic activity of a mature mutansucrase protein, and at least of 3%, preferred at least of 25%, more preferred at least of 45%, most preferred at least of 65% when genetically modified plant cells or genetically plants show an enzymatic activity of a catalytically active truncated mutansucrase protein.

In conjunction with the invention, the starch granule morphology can be determined by light microscopy (LM) and scanning electron microscopy (SEM) as described in the general methods (method 5).

In conjunction with the invention, a starch with an altered granule morphology can be defined as a starch having more than 5% of altered starch granules.

In conjunction with the invention, an altered starch granule is defined as a starch granule exhibiting an uncommon shape when compared to the great majority of the starch granules synthesized by wild-type plant cells. As examples, altered starch granules are starch granules with protruded forms, starch granules with eroded forms, small starch granules associated to larger ones, starch granules with pores in the surface and/or starch granules with a rough or uneven surface.

Preferably more than 10%, more preferably more than 15%, and still more preferred more than 20% of the starch granules isolated from genetically modified plant cells of the invention or genetically plants of the invention which show an enzymatic activity of a mature mutansucrase protein or an enzymatic activity of a catalytically active truncated mutansucrase protein show an altered morphology, in comparison to starch granules isolated from corresponding non-genetically modified wild-type plant cells or non-genetically modified wild-type plants, respectively.

Further, the present invention relates to genetically modified plant cells or genetically modified plants of the invention characterized in that said plant cells or said plants, respectively, synthesize a modified starch with an increase of the gel strength, in comparison to starch synthesized by wild-type plant cells or wild-type plants.

In conjunction with the invention, the gel strength (or gel formation properties of the glues) of the starch can be measured by the method described in general methods (method 3) of the present invention.

Preferably, the increase of the gel strength is 10%-600%, preferred 20%-500%, more preferred 25%-400% and most preferred 30%-300% when genetically modified plant cells or genetically plants show an enzymatic activity of a mature or catalytically active truncated mutansucrase protein.

It was found that genetically modified plant cells of the invention or genetically modified plants of the invention which show an enzymatic activity of a catalytically active truncated mutansucrase protein in their plastids synthesize a new type of starch granules to which mutan is attached.

The attachment of mutan to starch can be observed by staining starch granules with a erythrosine red colouring agent, as disclosed in general methods (method 5). Such colouring reaction is routinely used by oral specialists to demonstrate the presence of dental plaque.

Therefore further objects of the invention are genetically modified plant cells of the invention or genetically modified plants of the invention which show an enzymatic activity of a catalytically active truncated mutansucrase protein in their plastids characterized in that said genetically modified plant cells or genetically modified plants, respectively, synthesize starch granules to which mutan is attached. Preferred objects of the invention are genetically modified plant cells of the invention or genetically modified plants of the invention which show an enzymatic activity of a catalytically active mutansucrase protein wherein said plant cells or plants, respectively, synthesize starch granules to which mutan is attached wherein said starch granules are stainable by a erythrosine red coloring agent.

Furthermore, the invention relates to genetically modified plant cells according to the invention or genetically modified plants according to the invention, having integrated into its genome a transgene comprising linked to one another in a functional fashion in the direction of the transcription:
a promoter sequence which initiates transcription in plant cells,
a heterologous nucleic acid sequence encoding a mutansucrase protein or encoding a catalytically active truncated mutansucrase protein, and
optionally a termination sequence which is active in plant cells.

In conjunction with the invention the term "mutansucrase gene" is to be understood as a nucleic acid sequence encoding a mutansucrase protein.

In conjunction with the invention the term "truncated mutansucrase gene" is to be understood as a nucleic acid sequence encoding a catalytically active truncated mutansucrase protein.

An heterologous nucleic acid sequence encoding a catalytically active truncated mutansucrase gene can comprising nucleic acid sequences encoding only the active core region or can comprising nucleic acid sequences encoding the active core region and in addition nucleic acid sequences encoding amino acid sequences selected from the group consisting of
a) amino acid sequences constituting a full length or truncated variable region,
b) amino acid sequences constituting a full length or truncated C-terminal domain,
c) amino acid sequences constituting a truncated C-terminal domain and amino acid sequences constituting a full length variable region.
d) amino acid sequences constituting a full length C-terminal domain and amino acid sequences constituting a truncated variable region.
e) amino acid sequences constituting a truncated C-terminal domain and amino acid sequences constituting a truncated variable region.

A preferred catalytically active mutansucrase gene comprises the nucleic acid sequences which is at least 70%, preferably at least 80%, more preferably at least 90%, and especially preferably at least 95% with the nucleic acid sequence as identified under SEQ ID NO. 3.

Furthermore, the invention relates to genetically modified plant cells according to the invention or genetically modified plants according to the invention, having integrated into its genome a transgene comprising linked to one another in a functional fashion in the direction of the transcription:
a promoter sequence which initiates transcription in plant cells,
a heterologous nucleic acid sequence encoding a catalytically active truncated mutansucrase protein, and
optionally a termination sequence which is active in plant cells, wherein said genetically modified plant cells or genetically modified plants, respectively, synthesize a starch to which mutan is attached.

In conjunction with the present invention, the term "genome" is to be understood to mean the totality of the genetic material present in a plant cell. It is known to the person skilled in the art that, as well as the cell nucleus, other compartments (e.g. plastids, mitochondrions) also contain genetic material.

In a preferred embodiment, the transgene is integrated into the nuclear genome of the plant cell. Transport of the mutansucrase protein or the catalytically active truncated mutansucrase protein into a particular cellular compartment, such as plastid, may therefore be accomplished by the use of a transit peptide to target the cellular compartment of interest. The nucleic acid sequence encoding the transit peptide is inserted in front of the coding sequence. Sequences encoding a transit peptide may be derived from any nucleic acid sequence encoding a plant protein which is expressed in the cytoplasm and translocated to the cellular compartment of interest. The transit peptide can be identified by comparing the messenger RNA encoding the particular polypeptide with the amino acid sequence of the mature protein. The amino acid sequences absent from the mature protein and coded for by the corresponding messenger RNA beginning at the initiation codon, usually a methionine, will normally be the transit peptide, or will normally contain the transit peptide. The skilled person will be able to determine sequences encoding transit peptides using a program for prediction of transit peptide, as for example Chloro 1.1 Server (Emanuelsson O. et al, 1999, Protein Science:8:978-984)

The transit peptide is the amino acid sequence capable of directing a protein joined to the transit peptide to a cellular compartment of interest and may be the whole naturally occurring (wild-type) transit peptide, a functional fragment thereof, a functional mutant thereof, or a chimeric transit peptide wherein at least two transit peptides are associated to each other or of parts of different transit peptides associated to each other in a functional manner. Such a chimeric transit peptide is reported as an optimised transit peptide in EP0508909 and EP0924299.

The nucleic acid sequence encoding a transit peptide may be heterologous in respect to the nucleic acid sequence encoding the enzyme fused to it, meaning that the nucleic acid sequence encoding the transit peptide and the nucleic acid sequence encoding the enzyme to be directed to the plastids originate from different genes which again can originate from different species.

A transit peptide dedicated to target the enzyme translationally joined to it to a plastid, such as chloroplast or amyloplast, is called a plastidial transit peptide.

The present invention further relates to genetically modified plant cells of the invention or genetically modified plants of the invention having integrated into its genome a nucleic acid construct comprising linked to one another in a functional fashion in the direction of the transcription:
a promoter sequence which initiates transcription in plant cells,
a heterologous nucleic acid sequence encoding a plastidial transit peptide translationally fused with
a heterologous nucleic acid sequence encoding a mutansucrase protein or a catalytically active truncated mutansucrase protein, and optionally a termination sequence which is active in plant cells.

The term "linked to one another in a functional fashion" means that the elements of the nucleic acid construct are linked to one another in such a way which permits the expression of the coding region.

In conjunction with the invention the term "translationally fused" shall mean a fusion of nucleic acid sequences in such a way that they represent a single open reading frame, which upon transcription leads to the production of a single messenger RNA encoding a single protein, when translated.

Plastidial transit peptides may be selected from the group comprising the transit peptide of a gene encoding a waxy protein (Klösgen et al, Mol Gen Genet. 217 (1989), 155-161), the ribulose bisphosphate carboxylase small subunit (Wolter et al, Proc. Natl. Acad. Sci. USA 85 (1988), 846-850; Nawrath et al., Proc. Natl. Acad. Sci. 10 USA 91 (1994), 12760-12764), NADP-malate dehydrogenase (Gallardo et al., Planta 197 (1995), 324-332), Gluthation-reductase (Creissen et al., Plant J. 8 (1995), 167-175), EPSPS (U.S. Pat. No. 5,188,642), and an optimised transit peptide described in EP0508909 and EP0924299. These examples are not limitating.

In a preferred embodiment, a nucleic acid sequence encoding a plastidial transit peptide of the ferredoxin reductase gene (Pilon et al, 1995) is translationally fused with the nucleic acid sequence encoding a mutansucrase protein or a catalytically active truncated mutansucrase protein.

In another preferred embodiment, a nucleic acid sequence encoding the optimised plastidial transit peptide described in EP0508909 and EP0924299 is translationally fused with the nucleic acid sequence encoding a mutansucrase protein.

The technologies used for the construction of the nucleic acid sequence of the invention are well known to the skilled person. As non-limiting examples, it is possible to mention the technologies described in Sambrook et al. (Molecular Cloning, A Laboratory Manual, 3rd edition (2001) Cold Spring Harbour Laboratory Press, Cold Spring Harbour, N.Y. ISBN: 0879695773) and Ausubel et al. (Short Protocols in Molecular Biology, John Wiley & Sons; 5th edition (2002), ISBN: 0471250929).

Furthermore, plant and/or progeny thereof, which contain a plant cell according to the invention, are also the subject matter of the invention. Plants of this type can be produced from the plant cell according to the invention by regeneration, using methods known to the person skilled in the art, as for example methods described in "plant Cell Culture Protocols" 1999, edited by R. D. Hall, Humana Press, ISBN 0-89603-549-2.

In principle, the plants according to the invention can be plants of any plant species, i.e. both monocotyledonous and dicotyledonous plants. Preferably they are useful plants, i.e. plants, which are cultivated by people for the purposes of food or for technical, in particular industrial purposes.

In a further preferred embodiment, the plant according to the invention is a starch-storing plant. The term "starch-storing plants" includes all plants with starch-storing plant parts such as, for example, maize, rice, wheat, rye, oat, barley, cassava, potato, sago, mung bean, pea or sorghum. Preferred starch-storing plant parts are, for example, tubers, storage roots and grains containing an endosperm; tubers are particularly preferred; tubers of potato plants are especially preferred.

In a further preferred embodiment, the present invention relates to a starch-storing plant according to the invention which is a potato plant.

In conjunction with the present invention, the term "potato plant" or "potato" means plant species of the genus *Solanum*, in particular tuber-producing species of the genus *Solanum* and especially *Solanum tuberosum*.

The present invention also relates to propagation material of plants according to the invention containing a plant cell according to the invention.

Here, the term "propagation material" includes those constituents of the plant that are suitable for producing offspring by vegetative or sexual means. Cuttings, callus cultures, rhizomes or tubers, for example, are suitable for vegetative propagation. Other propagation material includes, for example, fruits, seeds, seedlings, protoplasts, cell cultures, etc. Preferably, the propagation material is seeds and particularly preferably tubers.

In a further embodiment, the present invention relates to harvestable plant parts of plants according to the invention such as fruits, storage roots, blooms, buds, shoots or stems, preferably seeds or tubers, wherein these harvestable parts contain plant cells according to the invention.

The present invention also relates to a method for the manufacture of genetically modified plants according to the invention wherein a) a plant cell is transformed with a nucleic acid molecule comprising a nucleic acid molecule encoding a mutansucrase protein or a catalytically active truncated mutansucrase protein, b) a plant is regenerated from a plant cell obtained in step a) and c) if necessary, further plants are produced from the plants obtained in step b).

The plant cell obtained in step a) may be regenerated to whole plants according to methods known to the skilled person, as for example using the methods described in "plant Cell Culture Protocols" 1999, edited by R. D. Hall, Humana Press, ISBN 0-89603-549-2.

In a preferred method for the manufacture of genetically modified plant of the invention the nucleic acid molecule encoding the mutansucrase protein or the catalytically active truncated mutansucrase protein in step a) is translationally fused with a nucleic acid molecule encoding a plastidial peptide sequence.

The production of further plants according to Step (c) of the method according to the invention can be carried out, for example, by vegetative propagation (for example using cuttings, tubers or by means of callus culture and regeneration of whole plants) or by sexual propagation. Here, sexual propagation preferably takes place under controlled conditions, i.e. selected plants with particular characteristics are crossed and propagated with one another.

The present invention also relates to a method for the manufacture of a genetically modified plant according to the method disclosed above, wherein the nucleic acid molecule encoding a mutansucrase protein or a catalytically active truncated mutansucrase protein is integrated into the plastidial genome of the plant.

The nucleic acid molecule encoding a mutansucrase protein may be from any desired origin, preferably the nucleic acid molecule encoding a mutansucrase protein originates form bacteria expressing such proteins.

More preferably, nucleic acid molecules used in the invention may encode a mutansucrase protein from a bacteria selected from the group consisting of *Streptococcus* bacteria.

Most preferably, nucleic acid molecules used in the invention may encode a mutansucrase protein from *Streptococcus downei* MFe28.

The nucleic acid molecule encoding a catalytically active truncated mutansucrase protein can be produced from any nucleic acid molecule encoding a mutansucrase protein by means of methods generally known by a person skilled in the field of molecular biology. Methods suitable for the manufacture of nucleic acid sequences encoding a catalytically active truncated mutansucrase protein are described e.g. in Sambrok et al. (Molecular Cloning, A Laboratory Manual, 3rd edition (2001) Cold Spring Harbour Laboratory Press, Cold Spring Harbour, N.Y. ISBN: 0879695773) and Ausubel et al. (Short Protocols in Molecular Biology, John Wiley & Sons; 5th edition (2002), ISBN: 0471250929). These methods include but are not limited to the manufacture of deletion mutants. of a nucleic acid sequence encoding a mutansucrase protein by use of restriction enzymes and/or the use of site directed mutagenesis (e.g. insertion of premature stop codons) and/or PCR amplification (e.g. of parts of the sequence encoding a mutansucrase protein) and/or chemical synthesis of parts of nucleic acid sequences encoding a mutansucrase protein in combination with ligation of the respective sequences to obtain a nucleic acid molecule which encodes a catalytically active truncated mutansucrase protein.

Nucleic acid molecules encoding a mutansucrase protein used in the invention may be isolated e.g. from genomic DNA or DNA libraries produced from any origin, preferably from bacteria. Alternatively, they may have been produced by means of recombinant DNA techniques. (e.g. PCR) or by means of chemical synthesis. The identification and isolation of such nucleic acid molecules may take place by using the molecules according to the invention or parts of these molecules or, as the case may be, the reverse complement strands of these molecules, e.g. by hybridization according to standard methods (see e.g. Sambrok et al., Molecular Cloning, A Laboratory Manual, 3rd edition (2001) Cold Spring Harbour Laboratory Press, Cold Spring Harbour, N.Y. ISBN: 0879695773) and Ausubel et al., Short Protocols in Molecular Biology, John Wiley & Sons; 5th edition (2002),ISBN: 0471250929)

As a probe for hybridization e.g. nucleic acid molecules may be used which exactly or basically contain the nucleotide sequences indicated under SEQ ID No. 1 or parts thereof. The fragments used as hybridization probe may also be synthetic fragments which were produced by means of the conventional synthesizing methods and the sequence of which is basically identical with that of a nucleic acid molecule according to the invention.

The molecules hybridizing to the nucleic acid molecules used in the invention also comprise fragments, derivatives and allelic variants of the above-described nucleic acid molecules which encode a mutansucrase protein. In this context, fragments are defined as parts of the nucleic acid molecules, which are long enough in order to encode proteins. In this context, the term derivatives means that the sequences of these molecules differ from the sequences of the above-mentioned nucleic acid molecules at one or more positions and that they exhibit a high degree of homology to these sequences. Homology means a sequence identity of at least 70% and still more preferably a sequence identity of more than 90% and most preferably a sequence identity of more than 95%. The deviations occurring when comparing with the above-described nucleic acid molecules might have been caused by deletion, substitution, insertion or recombination.

Moreover, homology means that functional and/or structural equivalence exists between the respective nucleic acid molecules or the proteins they encode. The nucleic acid molecules, which are: homologous to the above-described molecules and represent derivatives of these molecules, are generally variations of these molecules, that constitute modifications which exert the same biological function: These variations may be naturally occurring variations, for example sequences derived from other bacteria, or mutations, whereby these mutations may have occurred naturally or they may have been introduced by means of a specific mutagenesis. Moreover the variations may be synthetically produced sequences. The allelic variants may be naturally occurring as well as synthetically produced variants or variants produced by recombinant DNA techniques.

In a preferred embodiment of the present invention the nucleic acid molecules encoding a mutansucrase protein is chosen from the group consisting of:
a) Nucleic acid molecules, which encode a protein with the amino acid sequence given under SEQ ID NO: 2 or parts thereof, having the capability of catalysing the synthesis of mutan from sucrose;
b) Nucleic acid molecules, which encode a protein, the amino acid sequence of which has an identity of at least 70% with the amino acid sequence given under SEQ ID NO: 2 or parts thereof, having the capability of catalysing the synthesis of mutan from sucrose;
c) Nucleic acid molecules, comprising the nucleotide sequence shown under SEQ ID NO: 1 or a complementary sequence thereof, or parts thereof encoding protein having the capability of catalysing the synthesis of mutan from sucrose;
d) Nucleic acid molecules, the nucleic acid sequence of which has an identity of at least 70% with the nucleic acid sequences described under a) or c);
e) Nucleic acid molecules, the nucleotide sequence of which deviates from the sequence of the nucleic acid molecules identified under a), b), c) or d) due to the degeneration of the genetic code; and
f) Nucleic acid molecules, which represent fragments, allelic variants and/or derivatives of the nucleic acid molecules identified under a), b), c), d) or e).

In a further preferred embodiment of the invention, the nucleic acid molecules encoding a mutansucrase protein encode a protein, the amino acid sequence of which has an identity of at least 70%, preferably at least 80%, more preferably at least 90%, and still more preferably at least 95% to the amino acid sequence identified under SEQ ID NO: 2, or parts thereof, having the capability of catalysing the synthesis of mutan from sucrose.

In an other further preferred embodiment, the nucleic acid molecule encoding a mutansucrase protein has a nucleic acid sequence with an identity of at least 70%, preferably at least 80%, more preferably at least 90%, and still more preferably at least 95% to the sequence SEQ ID NO: 1 or parts thereof encoding a protein having the capability of catalysing the synthesis of mutan from sucrose.

In a further preferred embodiment of the present invention the nucleic acid molecules encoding a catalytically active mutansucrase protein is chosen from the group consisting of:
a) Nucleic acid molecules, which encode a protein with the amino acid sequence given under SEQ ID NO: 4 or parts thereof, having the capability of catalysing the synthesis of mutan from sucrose;
b) Nucleic acid molecules, which encode a protein, the amino. acid sequence of which has an identity of at least 70% with the amino acid sequence given under SEQ ID NO: 4 or parts thereof, having the capability of catalysing the synthesis of mutan from sucrose;
c) Nucleic acid molecules, comprising the nucleotide sequence shown under Seq ID SEQ ID NO 3 or a complementary sequence thereof, or parts thereof encoding protein having the capability of catalysing the synthesis of mutan from sucrose;

d) Nucleic acid molecules, the nucleic acid sequence of which has an identity of at least 70% with the nucleic acid sequences described under a) or c);

e) Nucleic acid molecules, the nucleotide sequence of which deviates from the sequence of the nucleic acid molecules identified under a), b), c) or d) due to the degeneration of the genetic code; and f) Nucleic acid molecules, which represent fragments, allelic variants and/or derivatives of the nucleic acid molecules identified under a), b), c), d) or e).

In a further preferred embodiment of the invention, the nucleic acid molecules encoding a catalytically active truncated mutansucrase protein encode a protein, the amino acid sequence of which has an identity of at least 70%, preferably at least 80%, more preferably at least 90%, and still more preferably at least 95% to the amino acid sequence identified under or SEQ ID NO: 4, or parts thereof, having the capability of catalysing the synthesis of mutan from sucrose.

Preferred parts of nucleic acid molecules encoding a mutansucrase protein are nucleic acid molecules encoding a protein having an identity of at least 70%, preferably at least 80%, more preferably at least 90%, and still more preferably at least 95% to the amino acid sequence as identified under SEQ ID NO: 4 from position 109 to 1012.

In an other further preferred embodiment, the nucleic acid molecule encoding a catalytically active truncated mutansucrase protein has a nucleic acid sequence with an identity of at least 70%, preferably at least 80%, more preferably at least 90%, and still more preferably at least 95% to the sequence SEQ ID NO: 3 or to the sequence as identified under SEQ ID NO: 3 from position 325 to 3036.

In conjunction with the present invention, the term "identity" is to be understood to mean the number of amino acids/nucleotides corresponding with the amino acids/nucleotides of other protein/nucleic acid, expressed as a percentage. Identity is preferably determined by comparing the Seq. ID NO: 1, SEQ ID NO: 2, SEQ ID NO: 3, SEQ ID NO: 4, or parts thereof with other protein/nucleic acid with the help of computer programs. If sequences that are compared with one another have different lengths, the identity is to be determined in such a way that the number of amino acids, which have the shorter sequence in common with the longer sequence, determines the percentage quotient of the identity. Preferably, identity is determined by means of the computer program ClustalW, which is well known and available to the public (Thompson et al., Nucleic Acids Research 22 (1994), 4673-4680). ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from different Internet sites, including the IGBMC (Institut de Génétique et de Biologie Moléculaire et Cellulaire, B. P. 163, 67404 Illkirch Cedex, France; ftp://ftp-igbmc.u-strasbg.fr/pub/) and the EBI (ftp://ftp.ebi.ac.uk/pub/software/) as well as from all mirrored Internet sites of the EBI (European Bioinformatics Institute, Wellcome Trust Genome Campus, Hinxton, Cambridge CB10 1SD, UK).

Preferably, Version 1.8 of the ClustalW computer program is used to determine the identity between proteins according to the invention and other proteins. In doing so, the following parameters must be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Preferably, Version 1.8 of the ClustalW computer program is used to determine the identity between the nucleotide sequence of the nucleic acid molecules according to the invention, for example, and the nucleotide sequence of other nucleic acid molecules. In doing so, the following parameters must be set:

KTUPLE=2, TOPDIAGS=4, PAIRGAP=5, DNAMATRIX:IUB, GAPOPEN=10, GAPEXT=5, MAXDIV=40, TRANSITIONS: unweighted.

Furthermore, identity means that functional and/or structural equivalence exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. For this purpose, modifications occur on amino-acid residues not involved in the enzyme activity. At the same time, the variations can occur naturally, for example they can be sequences from other bacterial species, or they can be mutations, wherein these mutations may have occurred in a natural manner or have been introduced by objective mutagenesis. The variations can also be synthetically manufactured sequences. The allelic variants can be both naturally occurring variants and also, synthetically manufactured variants or variants produced by recombinant DNA techniques. Nucleic acid molecules, which deviate from nucleic acid molecules according to the invention due to degeneration of the genetic code, constitute a special form of derivatives.

The use of nucleic acid molecules that encode a mutansucrase protein or a catalytically active truncated mutansucrase protein and the sequence of which differs from the nucleotide sequences of the above-mentioned nucleic acid molecules due to the degeneracy of the genetic code are also the subject-matter of the invention.

The invention also relates to the use of nucleic acid molecules showing a sequence which is complementary to the whole or to a part of one of the above-mentioned nucleic acid molecules.

For expressing nucleic acid molecules described above, these are preferably linked with regulatory DNA sequences, which guarantee initiation of transcription in plant cells. In particular, these include promoters. In general, any promoter that is active in plant cells is eligible for expression.

At the same time, the promoter can be chosen so that expression takes place constitutively or only in a certain tissue, at a certain stage of the plant development or at a time determined by external influences. The promoter can be homologous or heterologous both with respect to the plant and with respect to the nucleic acid molecule.

Suitable promoters are, for example, the promoter of the 35S RNA of the cauliflower mosaic virus and the ubiquitin promoter from maize for constitutive expression, the patatin promoter B33 (Rocha-Sosa et al., EMBO J. 8 (1989), 23-29) for tuber-specific expression in potatoes or a promoter, which only ensures expression in photosynthetically active tissues, e.g. the ST-LS1 promoter (Stockhaus et al., Proc. Natl. Acad. Sci. USA 84 (1987), 7943-7947; Stockhaus et al., EMBO J. 8 (1989), 2445-2451) or, for endosperm-specific expression of the HMG promoter from wheat, the USP promoter, the phaseolin promoter, promoters of zein genes from maize (Pedersen et al., Cell 29 (1982), 1015-1026; Quatroccio et al., Plant Mol. Biol. 15 (1990), 81-93), glutelin promoter (Leisy et al., Plant Mol. Biol. 14 (1990), 41-50; Zheng et al., Plant J.

4 (1993), 357-366; Yoshihara et al., FEBS Lett. 383 (1996), 213-218) or shrunken-1 promoter (Werr et al., EMBO J. 4 (1985), 1373-1380). However, promoters can also be used, which are only activated at a time determined by external influences (see for example WO 9307279). Promoters of heat-shock proteins, which allow simple induction, can be of particular interest here. Furthermore, seed-specific promoters can be used, such as the USP promoter from *Vicia faba*, which guarantees seed-specific expression in *Vicia faba* and other plants (Fiedler et al., Plant Mol. Biol. 22 (1993), 669-679; Bäumlein et al., Mol. Gen. Genet. 225 (1991), 459-467).

Promoters which are active in plastids of plant cells may be used if the nucleic acid construct of the invention is integrated in the plastidial genome of the plant cell. Among the promoters active in plastids of plant cells, by way of example, special mention can be made of the psbA gene which encodes the D1 polypeptide of PSII (Staub et al. 1993 EMBO Journal 12(2): 601-606), and the constitutive Prm promoter which regulates the ribosomal RNA operon (Staub et al. 1992 Plant Cell 4:39-45).

Furthermore, a termination sequence (polyadenylation signal) can be present, which is used for adding a poly-A tail to the transcript. A function in the stabilisation of the transcripts is ascribed to the poly-A tail. Elements of this type are described in the literature (cf. Gielen et al., EMBO J. 8 (1989), 23-29) and can be exchanged at will.

Plants obtainable by the method of the invention for the manufacture of a plant according to the invention are a further embodiment of the invention.

Furthermore, the invention relates to vectors, especially plasmids, cosmids, viruses, bacteriophages and other vectors common in genetic engineering, which contain the above-mentioned nucleic acid molecules encoding a mutansucrase protein or a catalytically active truncated mutansucrase protein. Such vectors are preferably vectors which can be used for the transformation of plant cells. More preferably, they allow for the integration of the nucleic acid molecules of the invention into the s nuclear or plastidial genome of the plant cell, if necessary in combination with flanking regulatory regions. Examples are binary vectors which may be used in the *Agrobacterium*-mediated gene transfer, as for example pBIN20 binary vector (Hennegan and Danna, 1998). Examples of vectors which may be used for direct plastid transformation are given in WO 04/055191.

The plasmid comprising the heterologous nucleic acid molecule to be introduced into the plant further can contain either a selectable marker or a reporter gene or both to facilitate identification and selection of transformed cells. Alternatively, the selectable marker may be carried on a separate vector and used in a co-transformation procedure. Both selectable markers and reporter genes may be flanked with appropriate regulatory sequences to enable expression in plants. Useful selectable markers and reporter genes are well known in the art and include, for example, antibiotic and herbicide resistance genes, genes encoding beta-glucuronidase enzyme (Staub et al, 1993) or green fluorescent protein (Sidorov et al, 1999). Specific examples of such genes are disclosed in Weising et al, 1988, Svab et al, 1993, White et al., Nucleic Acid Res. 18(4):1062.

By using the nucleic acid molecule encoding a mutansucrase protein or a catalytically active truncated mutansucrase protein, it is now possible—by means of recombinant DNA techniques—to interfere with the starch metabolism of plant cells or plants in a way so far impossible. Thereby, the starch metabolism may be modified in such a way that a modified starch is synthesized which e.g. is modified, compared to the starch synthesized in corresponding non-genetically modified wild type plant cells or non-genetically modified wild type plants, respectively, in its physico-chemical properties, the pastification behavior, the size and/or the shape of the starch granule. Compared with wild-type starch, such starch may be modified in particular with respect to its viscosity and/or the gel formation properties of the glues of this starch and/or its gel stability and/or its capability to be digested and/or the starch granule morphology.

The present invention therefore also relates to modified starches obtainable from plant cells according to the invention or plants according to the invention, from propagation material according to the invention or from harvestable plant parts according to the invention.

A further object of the invention is starch of the invention to which mutan is attached. Preferably the invention relates to modified starch granules to which mutan is attached wherein the starch granules are stainable with a erythosine red coloring agent. This starch is obtainable from genetically modified plant cells or genetically modified plants showing an activity of a catalytically active truncated mutansucrase protein in their plastids.

Preferred starch of the invention concerns starch from starch-storing plants of the invention such as, for example, maize, rice, wheat, rye, oat, barley, cassava, potato, sago, mung bean, pea or sorghum. Especially preferred is starch of potato plants.

The present invention further relates to a method for the manufacture of a modified starch comprising the step of extracting the starch from a plant cell according to the invention, from a plant according to the invention, from harvestable parts of a plant according to the invention, or from a plant obtainable by means of a method of the invention for the manufacture of a plant according to the invention.

Preferably, such a method also comprises the step of harvesting the cultivated plants and/or starch-storing parts of such plants before extracting the starch. Most preferably, it further comprises the step of cultivating the plants of the invention before harvesting. Methods for the extraction of starch from plants or from starch-storing parts of plants are known to the skilled person. Methods for the extraction of starch from maize seeds have been described e.g. in Eckhoff et al. (Cereal Chem. 73 (1996) 54-57). The extraction of starch on an industrial level is usually achieved by the so-called wet-milling technique. Furthermore, methods for the extraction of starch from various other starch-storing plants have been described, e.g. in "Starch: Chemistry and Technology (Editor: Whistler, BeMiller and Paschall (1994), 2.sup.nd edition, Academic Press Inc. London Ltd; ISBN 0-12-746270-8; see e.g. chapter XII, page 412-468: maize and sorghum starches: production; by Watson; chapter XIII, page 469-479: tapioca, arrowroot and sago starches: production; by Corbishley and Miller; chapter XIV, page 479-490: potato starch: production and use; by Mitch; chapter XV, page 491 to 506: wheat starch: production, modification and use; by Knight and Oson; and chapter XVI, page 507 to 528: rice starch: production and use; by Rohmer and Klem). Appliances generally used for extracting starch from plant material are separators, decanters, hydrocyclones, spray dryers and cyclon driers. Preferably, the method for the manufacture of a modified starch of the present invention comprises the steps described in example 3.

Due to the expression of a nucleic acid molecule encoding a mutansucrase protein or a catalytically active truncated mutansucrase protein, the transgenic plant cells and plants described in the invention synthesize a starch which compared to starch synthesized in corresponding non-genetically modified wildtype plant cells or non-genetically modified wildtype plants, respectively, is modified for example in its physico-chemical properties, the pastification behavior, the size and/or the shape of the starch granule. Compared with wildtype-starch, such starch may be modified in particular with respect to its viscosity and/or the gel formation properties of the glues of this starch and/or its gel stability and/or its capability to be digested and/or the starch granule morphology.

In a further embodiment of the invention the methods for the manufacture of a modified starch of the invention are used for the production of a modified starch of the invention.

Thus, also the modified starch obtainable from the method for the manufacture of a modified starch according to the invention is the subject-matter of the present invention.

In a preferred embodiment of the invention the starch of the invention is a native starch.

In conjunction with the present invention, the term "native starch" means that the starch is isolated from plants according to the invention, harvestable plant parts according to the invention or propagation material of plants according to the invention by methods known to the person skilled in the art.

The person skilled in the art knows that the characteristics of starch can be changed by thermal, chemical, enzymatic or mechanical derivation, for example. Derived starches are particularly suitable for different applications in the foodstuffs and/or, non-foodstuffs sector. The starches according to the invention are better suited as a starting substance for the manufacture of derived starches than conventional starches.

The present invention therefore also relates to a method for the production of a derived starch, wherein modified starch according to the invention or obtainable by means of a method according to the invention is derived retrospectively.

In conjunction with the present invention, the term "derived starch" is to be understood to mean a modified starch according to the invention, the characteristics of which have been changed after isolation from vegetable cells with the help of chemical, enzymatic, thermal or mechanical methods. In a preferred embodiment of the present invention, the derived starch according to the invention is starch that has been heat-treated and/or acid-treated.

In a further preferred embodiment, the derived starches are starch ethers, in particular starch alkyl ethers, O-allyl ethers, hydroxylalkyl ethers, O-carboxylmethyl ethers, nitrogen-containing starch ethers, phosphate-containing starch ethers or sulphur-containing starch ethers.

In a further preferred embodiment, the derived starches are cross-linked starches.

In a further preferred embodiment, the derived starches are starch graft polymers.

In a further preferred embodiment, the derived starches are oxidised starches.

In a further preferred embodiment, the derived starches are starch esters, in particular starch esters, which have been introduced into the starch using organic acids. Particularly preferably these are phosphate, nitrate, sulphate, xanthate, acetate or citrate starches.

Methods for manufacturing derived starches according to the invention are known to the person skilled in the art and are adequately described in the general literature. An overview on the manufacture of derived starches can be found, for example, in Orthoefer (in Corn, Chemistry and Technology, 1987, eds. Watson und Ramstad, Chapter 16, 479-499).

Derived starch obtainable by the method for the production of a derived starch according to the invention for manufacturing a derived starch is also the subject matter of the present invention.

A further embodiment of the invention is the use of modified starch according to the invention for the production of a derived starch.

The invention also relates to the use of a plant cell according to the invention, a plant according to the invention, harvestable parts of a plant according to the invention or a plant obtainable by means of a method of the invention, for the production of a modified starch.

The invention also relates to the use of a nucleic acid molecule encoding a mutansucrase protein or a catalytically active truncated mutansucrase protein for the manufacture of a genetically modified plant cell according to the invention, a genetically modified plant according to the invention, propagation material according to the invention, or harvestable parts of plants according to the invention.

Furthermore the use of a nucleic acid sequence encoding a mutansucrase protein or a catalytically active truncated mutansucrase protein for the production of a modified starch according to the invention is an embodiment of the invention.

General Methods:

Method 1: Determination of the Viscosity Characteristics by Means of a Rapid Visco Analyser (RVA).

2 g of potato starch (for other types of starch or flour to be used, the values should be adjusted according to the manufacturers manual) are taken up in 25 ml of $H_2O$ (VE-type water, conductivity of at least 15 mega ohm) and used for the analysis in a Rapid Visco Analyser Super3 (Newport Scientific Pty Ltd., Investmet Support Group, Warriewod NSW 2102, Australia). The apparatus is operated following the manufacturer's instructions. The viscosity values are indicated in Centipoise (cP) in accordance with the manufacturer's operating manual, which is incorporated into the description herewith by reference. To determine the viscosity of the aqueous starch solution, the starch suspension is first stirred for 10 seconds at 960 rpm and subsequently heated at 50° C. at a stirring speed of 160 rpm, initially for a minute (step 1). The temperature was then raised from 50° C. to 95° C. at a heating rate of 12° C. per minute (step 2). The temperature is held for 2.5 minutes at 95° C. (step 3) and then cooled from 95° C. to 50° C. at 12° C. per minute (step 4). In the last step (step 5), the temperature of 50° C. is held for 2 minutes. The viscosity is determined during the entire duration.

After the program has ended, the stirrer is removed and the beaker covered. The gelatinized starch is now available for the texture analysis after 24 hours incubation at room temperature.

The profile of the RVA analysis contains parameters which are shown for the comparison of different measurements and substances. In the context of the present invention, the following terms are to be understood as follows:

1. Maximum viscosity (RVA Max) or peak viscosity

The maximum viscosity is understood as meaning the highest viscosity value, measured in cP, obtained in step 2 or 3 of the temperature profile.

2. Minimum viscosity (RVA Min) or valley viscosity

The minimum viscosity is understood as meaning the lowest viscosity value, measured in cP, observed in the temperature profile after the maximum viscosity. Normally, this takes place in step 3 of the temperature profile.

3. Final viscosity (RVA Fin) or end viscosity

The final viscosity (or end viscosity) is understood as meaning the viscosity value, measured in cP, observed at the end of the measurement.

4. Setback (RVA Set)

What is known as the "setback" is calculated by subtracting the value of the final viscosity from that of the minimum occurring after the maximum viscosity in the curve.

5. Gelatinization temperature (RVA PT) or T-onset temperature

The gelatinization temperature is understood as meaning the point in time of the temperature profile where, for the first time, the viscosity increases drastically for a brief period.

Method 2 Determination of the Viscometric Profiles by Means of a Thermo Haake Rheoscope.

Viscometric profiles from a 2% starch suspension were determined by applying a small oscillating shear deformation at a frequency of 1 Hz, using a Thermo Haake rheoscope. The rheometer was equipped with parallel plate geometry (typ C70/1 Ti) and the gap size was 0.1 mm. The pasting profile of the 2% starch-water (w/v) suspension was obtained by heating the suspension from 40° C. to 90° C. at a rate of 2° C./min, where it was kept for 15 min followed by cooling to 20° C. at a rate of 2° C./min and hold again for 15 min at 20° C. The Tg (gelatinization temperature or T-onset temperature), Tp (peak temperature) and viscosities were measured. Subsequently, from the retrograded sample, an amplitude sweep was run at 10 Pa increasing to 1.000 Pa within 60 s to check that the measurements were made in the linear region, in which the amplitudes of stress and strain are proportional to each other.

Method 3: Determination of the Gel Formation Properties of the Glues of the Starch by Means of a Texture Analyser TA-XT2.

The sample is gelatinized in the RVA apparatus in an aqueous suspension by means of a Rapid Visco Analyser (RVA) according to the method described above (method 1) and subsequently stored for 24 hours at room temperature in a sealed container. The samples are fixed under the probe (round piston with planar surface) of a Texture Analyser TA-XT2 from Stable Micro Systems (Surrey, UK) and the gel strength was determined using the following parameters:

| Test speed | 0.5 mm/s |
|---|---|
| Depth of penetration | 7 mm |
| Contact surface | 113 mm2 |
| Pressure | 2 g. |

Method 4: Determination of Digestibility of Starch Based on the Determination of Resistant Starches RS Type III.

Resistant starches, RS, can be divided into the following types:
RS type 1 Starch not accessible physically to digestion, for example partly milled plant cells (e.g. in muesli).
RS type 2 Indigestible granular starch (starch grains), for example from raw potatoes, green bananas, etc.
RS type 3 Indigestible retrograded starch that is obtained, for example, by thermal and/or enzymatic treatment and then retrograded.
RS type 4 Indigestible, chemically modified starch that is formed, for example, by cross-bonding or esterification (acetylation, etc).

The determination of resistant starches RS Type III was obtained using the following steps:
 a) Pancreatine/Amyloglucosidase (AGS) Treatment
 Pancreatine/amyloglucosidase digestion buffer used:
 0.1 M Na acetate pH 5.2
 4 mM CaCl2
 Preparation of the enzyme solution:
 12 g pancreatine (Merck, Product no. 1.07130.1000) were stirred in 80 ml demineralised water (conductivity ca. 18 M ohm) for 10 min at 37° C. and then centrifuged for 10 min at 3000 rpm.

54 ml of the supernatant obtained after centrifugation were treated with 9.86 ml demineralised water and 0.14 ml amyloglucosidase (6000 u/ml, Sigma, Product no. A-3042).

Pancreatine/Amyloglucosidase (AGS) Digestion Procedure 5 assays of the pancreatine/amyloglucosidase (AGS) digestion are prepared each time for each batch starch to be measured. No enzyme solution is later added to 2 of each of these 5 assays. The assays to which no enzyme solution is added are designated as reference and are used for determination of the recovery rate. The remaining 3 assays are designated as sample, later treated with enzyme solution and used for the determination of the RS content.

A number of reaction vessels which contain no starch were processed in parallel (blank samples). These blank samples which contain no starch are used for the determination amount of co-precipitated material (protein, salts).

The tare weight of 50 ml reaction vessels (Falcon tubes) was determined and then in each case ca. 200 mg of the starch are weighed in.

15 ml Na acetate buffer was added to each of the linear water-insoluble poly-alpha-1,4-D-glucan samples and the blanks samples, and 20 ml Na acetate buffer to each of the references (see above). These samples were pre-warmed to 37° C.

The reaction was initiated by the addition of 5 ml enzyme solution to each of the individual reaction vessels of the samples and the blank samples which were then shaken for 2 hours at 37° C. (200 rpm).

The reaction was quenched by the addition of 5 ml glacial acetic acid (equilibrated to pH 3.0) and 80 ml technical ethanol to the samples, blank samples and the references.

Precipitation of the starch from the reaction mixture was achieved by incubation of the quenched reaction assay at room temperature for 1 hour. After sedimentation (centrifugation for 10 min at 2500×g) the sediment of the individual assays obtained was washed. twice with 80% ethanol to remove short-chain glucans and then freeze dried after cooling to −70° C. The samples were re-weighed and the weight differences used for the calculation of the "gravimetric" RS content.

b) Determination of the RS Content

The following procedure was used for the determination of RS content of the individual batches of water-insoluble starch:
 a) Determination of the water content of the individual sample batches of starch (wt.H2O)
 b) Determination of the tare weight of the individual reaction vessels for the respective samples (wt.RGP), references (wt.RGR) and the blank samples (wt.RGB).
 c) Weighing ca. 200 mg of water-insoluble starch into the individual reaction vessels for samples (wt.P) and references (wt.R)
 d) Calculation of the dry fraction of the weights for samples (wt.Ptr=wt.P−wt.H2O) and references (wt.Rtr=wt.P−wt.H2O)
 e) Enzymatic digestion of the respective samples and blank samples. References are treated in the same way but without addition of the enzyme solution.
 f) Precipitation, sedimentation, washing and freeze drying of the substances remaining in the reaction vessels of the samples, references and blank samples after the treatment described in e).
 g) Weighing of the substances remaining in the reaction vessels of the samples (wt.PRG), references (wt.RRG) and blank samples (wt.BRG), inclusive of reaction vessel after the treatment described in f).

h) Calculation of the weight of the substances remaining in the reaction vessels of the
samples (wt.Pnv=wt.PRG−wt.RGP),
references (wt.Rnv=wt.RRG−wt.RGR)
and the blank samples (wt.Bnv=wt.BRG−wt.RGB)
after the treatment described under f).
i) Determination of the water content of the substances remaining in the reaction vessels of
samples (wt.H2OPnv),
references (wt.H2ORnv)
and the blank samples (wt.H2OBnv)
after the treatment described under f).
j) Calculation of the dry fraction of the substances remaining in the reaction vessels of the
samples (wt.Pnvtr=wt.Pnv−wt.H2OPnv)
references (wt.Rnvtr=wt.Rnv−wt.H2ORnv)
and the blank samples (wt.Bnvtr=wt.Bnv−H2OBnv)
after the treatment described under f).
k) Determination of the corrected weights for the
samples (wt.Pnvkorr=wt.Pnvtr−wt.Bnvtr)
and references (wt.Rnvkorr=wt.Rnvtr−wt.Bnvtr)
l) Calculation of the percentage fraction of the corrected weights of the water-insoluble starch remaining after enzymatic digestion relative to the dry weight of the starting amount of the samples (RSaP=wt.Pnvkorr/wt.Ptr×100)
and calculation of the percentage fraction of the corrected weights of the remaining water-insoluble starch of the references relative to the dry weight of the starting amounts of the references (RSaR=wt.Rnvkorr/wt.Rtr×100).
m) Determination of the mean value of the percentage fractions of the water-insoluble starch remaining after enzymatic digestion of the samples (RSaPMW=n× RSaP/n)
and determination of the mean values of the percentage fractions of the remaining water-insoluble starch of the references: (recovery rate; RSaRMW=n×RSaR/n)
where n is the number of sample and reference assays carried out for the respective batches of water-insoluble starch.
n) Determination of the percentage RS content of the individual batches of water-insoluble starch by correction of the mean values of the percentage fractions of the water-insoluble starch remaining after enzymatic digestion with the recovery rate (RS=RSaPMW/RSaRMW×100).

Method 5: Determination of Morphological and Physicochemical Properties of Starch Granules Analysis of starch granule morphology was performed by light microscopy (LM) (Axiophot, Germany) equipped with a Sony colour video camera (CCD-Iris/RGB) and scanning electron microscopy (SEM, JEOL 6300F, Japan). For LM, the granules were stained with a 2× diluted Lugol solution before visualization. For SEM, dried starch samples spread on silver tape and mounted on a brass disk were coated with a 20 nm platinum layer. Samples were then examined with a scanning electron microscope operating at an accelerating voltage of 1.5-3.5 keV. The working distance was 9 mm. Mutan polymers were visualized with LM by staining starch granules with a 10×diluted erythrosine red colouring agent (Disclosing Red-Cote solution) (American Dental Trading BV, The Netherlands). Mutan polymers were produced in presence of sucrose by a mixture of streptococcal glucosyltransferase (*Streptococcus mutans* 20381, *S. mutans* 6067 and *S. sobrinus* 6070). serving as a positive control (Wiater. et al., 1999). Exo-mutanase (α 1,3-glucanase, EC 3.2.1.59) was produced by *Trichoderma harzianum* F-470 (Wiater and Szczodrak, 2002). Mutanase assays were performed with 0.025 U of exo-mutanase enzyme in 0.2 M sodium acetate buffer (pH 5.5) at 40° C. for 48 h in presence of 10 mg (transgenic) starch. After brief centrifugation (1 min; 10,000 g), the supernatant was discarded and the starch granules were stained with the erythrosine red colouring solution.

Method 6: SDS PAGE Assay of the Activity of the Mutansucrase and Staining

Protein extracts are prepared from plant tissue. Mutansucrase activity in the respective plant protein extracts are detected by SDS PAGE separation of the proteins (ca. 80 μg, of total plant protein) followed by SDS removal by washing with 50 mM sodium acetate buffer. pH 5.3 and incubation of the gels in 50 mM sodium acetate pH 5.3,.5% (w/v) sucrose at 37° C. for 16 hours (Miller and Robyt, Analytical Biochemistry 156, (1986), 357-363). After incubation with sucrose a white band appears at the position of the mutansucrase protein due to the fact that mutan is a water insoluble glucan. Additionally the SDS gel can be stained with an erythrosine red colouring agent as described above (method 5).

To further increase the sensitivity of the SDS PAGE Assay, Dextran T10 (around 5% to 10%) can be included in the incubation buffer containing sucrose.

The invention is specifically illustrated by the following examples which are not in any way limiting.

EXAMPLE 1

Preparation of Constructs Containing the Mature or the Truncated Mutansucrase Gene An expression cassette containing the patatin promoter (Wenzler et al., 1989), the chloroplastic ferredoxin signal peptide (FD) from *Silene pratensis* (Pilon et al., 1995) and the NOS terminator was cloned into the pBluescript SK(pBS SK) plasmid, resulting in pPF. A mature mutansucrase (GtfI) gene from *S. downei* Mfe28(Ferretti et al., 1987) was ligated in frame between the signal peptide FD and the NOS terminator. The mature GtfI gene was amplified by PCR, with a forward primer containing a SmaI restriction site (5'-AGCTTGCG-GCCCCGGGACTGAAAC-3') (SEQ ID NO: 5) and a reverse primer containing an EcoRI restriction site (5'-GTGGTG-GTGGAATTCGAGTTAGTTC -3') (SEQ ID NO: 6) using the proofreading Pfu turbo DNA polymerase (2.5 units/μl; Stratagene) and cloned into the SmaI/EcoRI restriction sites of pPF, resulting in pPFGtfI.FD and the fused GtfI gene were completely sequenced in one direction by Baseclear (The Netherlands) to verify the correctness of the construct. pPF-GtfI was digested with XhoI and ligated into a pBIN20 binary vector (Hennegan and Danna, 1998), resulting in pPFI.

For the construction of FD-GtfICAT-NOS fusion, comprising a truncated GtfI gene, the GTFI gene was amplified by PCR, with a forward primer containing a SmaI restriction site (5'-AGCTTGCGGCCCCGGGACTGAAAC -3') (SEQ ID NO: 5) and a reverse primer containing an EcoRI restriction site (5'-AGAAGGAATTCTCATCTTAAACATTGAG-GTA -3') (SEQ ID NO: 7) and cloned into the SmaI/EcoRI restriction sites of pPF, resulting in pPFGTFICAT. Sequencing and cloning into the Pbin20 binary vector, resulting in pPFICAT, were performed as for pPFI.

EXAMPLE 2

Transformation and Regeneration of Potato Plants pPFI and pPFICAT were transformed respectively into *Agrobacterium tumefaciens* strain LBA 4404 using electroporation (Takken et al., 2000). Internodal stem segments from the tetraploid potato genotype cv. Kardal (KD) were used for *Agrobacterium*-mediated transformation. Transformants were selected on plates with MS30 medium (Murashige and Skoog, 1962) containing kanamycin (100 mgA). 30 transgenic, root forming, shoots per construct were multiplied and were transferred to the greenhouse for tuber development. The mature tubers were harvested after 18 weeks.

Transformed potato plant series are referred to as KDIxx and KDICxx respectively, in which I and IC refer to the Gtfi and gtfiCAT genes respectively and xx to the clone number.

EXAMPLE 3

Starch Isolation

Potato tubers were peeled and homogenized in a Sanamat Rotor (Spangenberg, The Netherlands). The resulting homogenate was allowed to settle overnight at 4° C. and the potato juice was decanted and stored at −20° C. for characterization of soluble mutan polymers. The starch pellet was washed three times with water and finally air-dried at room temperature for at least three days. The dried starch was powdered and stored at room temperature.

EXAMPLE 4

Expression Analysis of Gtfi and GtfiCAT Genes using Semi-quantitative and Real-time Quantitative RT-PCR Analysis RNA was isolated from 3 g (fresh weight) of potato tuber material from selected transgenic lines according to Kuipers et al. (1994).

For semi-quantitative RT-PCR, 50 µg of total RNA was treated with DNAseI and purified using the Gene-elute mammalian total RNA kit (Sigma, The Netherlands). The reverse transcription was performed using 5 µg of total RNA which was incubated for 5 min at 65° C. with 500 ng primer polydT (5'-tttttttttttttttttttttttttt-3') (SEQ ID NO: 8) and 12.5 mM each dNTP in a final volume of 12 µl. After brief centrifugation (30 sec; 10,000 g), the mixture was incubated 2 min at 42° C. with 4µl of 5 x first-strand buffer (Invitrogen, The Netherlands) and 2 µl of 0.1 M DTT. 1 µl of SuperScript II Rnase $H^{13}$ reverse transcriptase (200 U/µl; Invitrogen) was added and the mixture was incubated 50 min at 42° C. Following this, the reaction was terminated by heating the sample for 15 min at 70° C. 2.5 µl of cDNA was used in a standard PCR reaction with the following primer/Tm/cycles number combinations as described as below. For each combinations, the cycle number was optimized in order to remain in the exponential phase. GtfIRT primers, 5'-CCGTGCTTACAGTACCTCAGC-3' (SEQ ID NO: 9) and 5'-GGTCGTTAGCATTGTAGGT-GAAA-3' (SEQ ID NO: 10) (Tm=59° C., 35 cycles) were based on the GtfI gene sequence (Ferretti et al., 1987). Ubi3 primers, 5'-GTCAGGCCCAATT'ACGAAGA-3' (SEQ ID NO: 11) and 5'-AAGTTCCAGCACCGCACTC-3' (SEQ ID NO: 12) (Tm=55° C., 40 cycles) were used as an internal control and were based on the ubiquitin-ribosomal protein gene sequence (Ubi3) from potato (Garbarino and Belknap, 1994).

RT-PCR was performed on a number of transformants that were divided in each serie KDI or KDIC respectively, in three classes, based on the band intensity of the different PCR products. The band intensities were compared to that of Ubi3, which was used as an internal control (Garbarino and Belknap, 1994). These transformants were therefore classified as (−), (+) or (++), where (−), (+) and (++) represent undetectable, intermediate and high levels of mRNA respectively. As expected, no Gtfl mRNA was detected in the KD-UT plants.

Further characterization was performed on transformants from the different classes for the KDI and KDIC series.

EXAMPLE 5

Impact of Mutan Expression on Starch Granule Morphology, on the Attachment of Mutan to Starch, on Plant Morphology, Tuber Number and Yield The morphology of starch granules was determined by SEM and LM as described in the general methods (method 5).

With both means (SEM and LM), the presence of altered starch granules was observed for the KDI and KDIC series. FIG. 1 shows the modified starch granule morphology observed by scanning electron microscopy analysis performed on the starch of selected potato plants transformed with the mature mutansucrase gene (KDI) or with a truncated mutansucrase gene (KDIC), compared to the starch of a wild type Kardal plant (Kardal).

Figure 2:
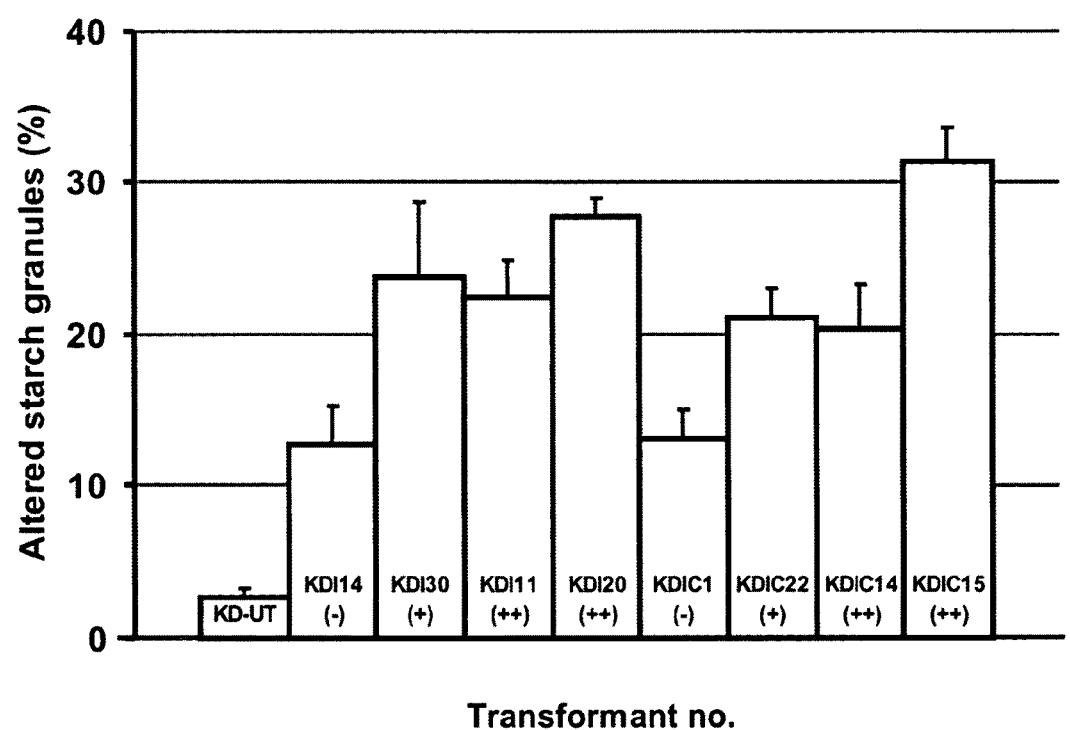
FIG. 2: Percentage of altered starch granules observed for untransformed plant (KD-UT) or for selected potato plants transformed with the mature mutansucrase gene [KDI14 (−), KDI30 (+), KDI11 (++), KDI20 (++)] or with a truncated mutansucrase gene [KDIC1 (−), KDIC22 (+), KDIC14 (++), KDIC15 (++)], wherein (−), (+) and (++) refers to the comparative level (undectectable, intermediate, and high respectively) of mRNA expressed for Gtfi or GtfiCAT genes.

For the KDI series, starches contained uncommonly shaped granules with protruded forms and with small granules that associated to larger ones. For the KDIC series, starches contained uncommonly shaped granules with eroded and protruded forms. In addition pores in the granule surface were often observed. Quantification of altered starch granules number were performed for each series by analysing a population of 100 starch granules in triplicates for transformants from each class (−) (+) and (++) defined via RT-PCR in example 4. FIG. 2 show the % of altered starch granules for an untransformed plant (KD-UT), for transformants of the different classes for the serie KDI [KDI14 (−), KDI30 (+), KDI11 (++) and KDI20 (++) respectively], and for transformants of the different classes for the serie KDIC [KDIC1 (−), KDIC22 (+), KDIC14 (++) and KDIC15 (++) respectively]. The percentage of altered starch granules was ranging from about 20% to about 30% for transformants exhibiting an intermediate or high levels of mutansucrase mRNA determined by RT-PCR. For transformed plants with an undetectable level of mRNA, the frequency of altered starch is about 13%. For untransformed plants, the frequency of altered starch is about 3%.

Figure 3:
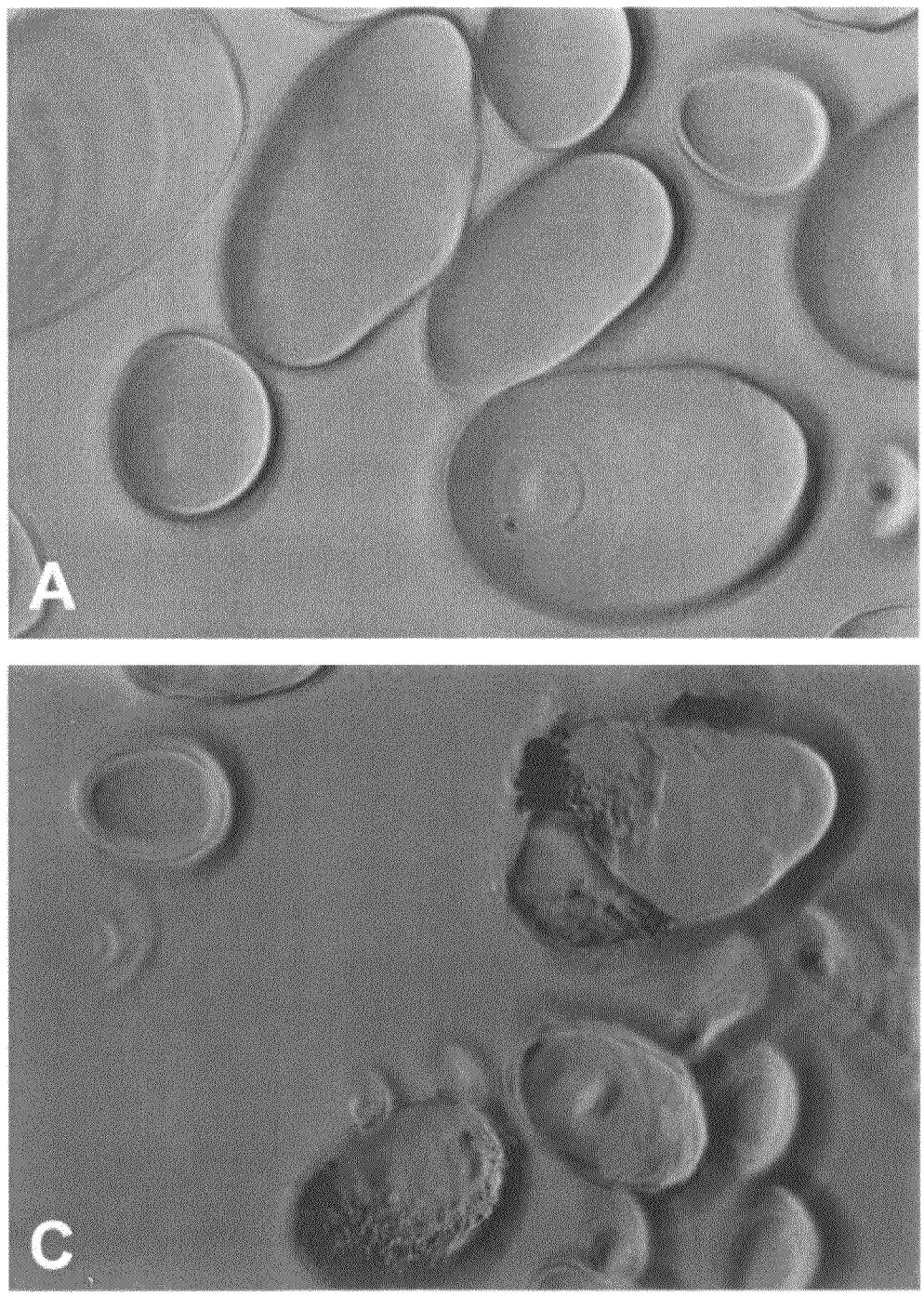
FIG. 3: Vizualization of mutan polymers attached to starch granules using an erythrosine red colouring solution. Mutan polymers are present on KDIC15 starch granules (FIG. 3.C). No colouration was observed for the KDI serie, which was comparable to KD-UT (FIG. 3.A).

An erythrosine red coloring solution was used for the visualization of mutan polymers attached to starch granules. As a positive control, mutan polymers (Wiater et al, 1999) were colored with this colouring agent. Interestingly, mutan polymers were present on KDIC serie transformants starch granules surfaces, in an attached or free form. FIG. 3 shows the colored mutan present on KDIC15 starch granule surfaces. No coloration was observed for the KDI serie transformants that were comparable to untransformed plants (FIG. 3). When KDIC transformant starch granules were treated with an exomutanase solution, most of the mutan polymers were detached from the starch granules. It might demonstrate that the binding only occurred superficially at the starch granule surface.

It could be possible that the non-attachment of mutan polymers to KDI starch, granules is due to the fact that mutan polymers with a lower molecular weight are produced, thereby limiting their adhesion to granules surfaces.

For the KDI and KDIC series, the tuber number, yield and plant morphology were unchanged and comparable to the untransformed plants.

EXAMPLE 7

Impact of Mutan Expression on the Viscosimetric Profile Determined by Means of a Thermo Haake Rheoscope The viscometric profiles from a starch suspension obtained from potato plants transformed with the mature mutansucrase gtfi gene (KDI) or with a truncated mutansucrase gtficat gene (KDIC) and from a wild-type Kardal plant (Kardal) have been determined by the mean of a Thermo Haake rheoscope, using the method described in the general methods (method 2).

The following table shows the increase in the T-onset temperature, minimum (valley) viscosity, and end viscosity, for the starch samples extracted from selected transformants (KDI or KDIC) compared to the starch of a wild-type Kardal plant (Kardal).

Kardal, KDI and KDIC: average values of two independent analyses, from a
2% starch solutions

| Starch Sample | T-Onset (° C.) | T-Peak (° C.) | Peak Viscosity (PaS) | Valley Viscosity (PaS) | End Viscosity (PaS) |
|---|---|---|---|---|---|
| Kardal | 73.7 | 75.4 | 117 | 21 | 110 |
| KDIC | 75.3 | 78.1 | 123 | 44 | 185 |
| KDI | 74.1 | 76.3 | 96 | 24 | 114 |

EXAMPLE 8

Impact of Mutan Expression on the Gel Formation Properties of the Glues

The gel formation properties of the glues (i.e. gel strength) is determined using the method detailed in the general methods (method 3) for starch suspensions obtained from potato plants transformed with the mature mutansucrase gtfi gene (Mutansucrase full length line 030), or with a truncated mutansucrase gtficat gene (Mutansucrase truncated line 014, lines 015, line 024) and from wild-type Kardal plants (Kardal 1 and Kardal 2).

The following table shows the increase of the gel strength for the starch samples extracted from the potato plants transformed with the mature or truncated mutansucrase gene compared to the starch extracted from wild-type Kardal plants.

|  | Gel strength (g) |
|---|---|
| Mutansucrase full length Line 030 | 51.0 |
| Mutansucrase truncated Line 014 | 64.0 |
| Mutansucrase truncated Line 015 White potatoes | 93.0 |
| Mutansucrase truncated Line 015 Brown potatoes | 73.0 |
| Mutansucrase truncated Line 024 | 48.0 |
| KARDAL1 | 36.0 |
| KARDAL2 | 38.0 |

EXAMPLE 9

Impact of Mutan Expression on Digestibility of Starch

The digestibility of starch has been determined using the method detailed in the general methods (method 4). The determination was based upon the method of Englyst (European Journal of Clinical Nutrition (1992) 46 (suppl. 2), p. 33-50) for the determination of resistant starches Type III, modified in correspondence with the information on the determination of RS content in WO 00 02926.

The following table show a decrease in the percentage of the digested starch for samples extracted from potato plants transformed with a truncated mutansucrase gene (KDIC) compared to the starch of a wild type Kardal plant (Kardal).

Percentage of digested starch (average) (%):

|  | 15 | 30 | 45 | 60 | 120 | 180 | 240 | 300 | 360 | min |
|---|---|---|---|---|---|---|---|---|---|---|
| Kardal | 3 | 5 | 7 | 9 | 15 | 21 | 26 | 31 | 37 |  |
| KDIC | 3 | 4 | 6 | 8 | 13 | 19 | 25 | 30 | 35 |  |

Kardal: average values from four independent measurements
KDIC: average values from four independent measurements All publications patent applications and patents referred to are herein incorporated by reference to the same extent as if each publication, patent application or patent was specifically and individually indicated to be incorporated by reference.

REFERENCES

An et al. EMBO J. 4, (1985), 277-287
Bäumlein et al., Mol. Gen. Genet. 225 (1991), 459-467
Chan. et al., Plant Mol. Biol. 22, (1993), 491-506;
van Cleve, J. W., Schaefer, W. C. and Rist, C. E. 1956. J. Am. Chem. Soc. 78: 4435-4438.
Conner and Domisse, Int. J. Plant Sci. 153 (1992), 550-555
Creissen et al., Plant J. 8 (1995), 167-175
De Vuyst and Degeest 1999 FEMS Microbiol Rev. 23 (2): 153-77.
Deng et al, Science in China 33, (1990), 28-34
Eckhoff et al. Cereal Chem. 73 (1996) 54-57
Emanuelsson O. et al, 1999, Protein Science:8:978-984
Englyst H. N. et al., European Journal of Clinical Nutrition 4, Suppl. 2, S33-S50
Ferretti et al., 1987
Fiedler et al., Plant Mol. Biol. 22 (1993), 669-679
Fraley et al., Crit. Rev. Plant Sci. 4, 1-46
Fromm et al., Biotechnology 8, (1990), 833-844;
Fu D, Robyt J F (1990) Carbohydr Res 183:97-109;
Fu D, Robyt J F (1990) Arch Biochem Biophys 283: 379-387
Garbarino and Belknap, 1994
Gallardo et al. (1995), Planta 197, 324-332
Gerrits, N., Turk, S. C. H. J., van Dun, K. P. M., Hulleman, S. H. D., Visser, R. G. F., Weisbeek, P. J. and Smeekens, S. C. M. 2001. Plant Physiol. 125: 926-934.
Gielen et al. 1989, EMBO J. 8, 23-29
Gordon-Kamm et al. 1990, Plant Cell 2, 603-618;
Hiei et al. (1994), Plant J. 6, 271-282
Hehre E J, Hamilton D M, Carlson A S (1949). J Biol Chem 177: 267-279
Hennegan, K. P. and Danna, K. J. (1998). Plant Mol. Biol. Rep. 16:129-131.
Hoekema, IN: The Binary Plant Vector System Offsetdrukkerij Kanters B. V., Alblasserdam (1985), Chapter V
Janecek S, Svensson B, Russell R R B (2000). FEMS Microbiol Left 192: 53-57
Jeanes, A., Haynes, W. C., Wilham, C. A., Rankin, J. C., Melvin, E. H., Austin, M. J., Cluskey, J. E., Fisher, B. E., Tsuchiya, H. M. and Rist, C. E. (1954). J. Am. Chem. Soc. 76: 5041-5052.

Khan M. S. and Maliga P. (1999). Nat. Biotechnol. 17, 910-915
Klösgen et al (1989), Mol Gen Genet. 217, 155-161
Kok-Jacob A., Ji Q., Vincken J P., and Visser R G. (2003) J. Plant Physiol; 160, 765-777
Kortstee A J, Vermeesch A M, de Vries B J, Jacobsen E, Visser R G. (1996), Plant J. 10(1):83-90.
Kossmann and Llyod (2000), Crit. Rev. Bioch. Mol. Biol. 35: 141-196
Koziel et al., (1993) Biotechnology 11, 194-200;
Krens et al., Nature 296, (1982), 72-74
Kuipers et al. (1994).
Leisy et al., Plant Mol. Biol. 14 (1990), 41-50
Loesche, 1986
MacGregor E A, Jespersen H M, Svensson B (1996). FEBS left 378: 263-266
Marsh, 2003
Matsuda, T. and Kabat, E. A. 1989. J. Immunol. 142: 863-870.
May et al., Bio/Technology 13, (1995), 486-492;
Monchois V, Remaud-Simeon M, Russell R R B, Monsan P and Willemot R M. 1997. Appl. Microbiol. Biotechnol. 48: 465-472
Monchois V, Remaud-Simeon M, Monsan P and Willemot R M. 1998. FEMS Microbiol. Lett. 159: 307-315
Monchois et al., 1999, FEMS Microbiology Letters 177, 243-248;
Monchois V, Willemot R M and Monsan P. 1999, FEMS Microbiology Reviews 23, 131-151.
Moroc et al., Theor. Appl. Genet. 80, (1990), 721-726).
Murashige, T. and Skoog, F. 1962. Physiol. Plant. 15: 473-497.
Nawrath et al., Proc. Natl. Acad. Sci. 10 USA 91 (1994), 12760-12764)
Nehra et al., Plant J. 5, (1994), 285-297
Oakes J V, Shewmaker C K, Stalker D M (1991). Biotechnol 9: 982-986
Pedersen et al., Cell 29 (1982), 1015-1026;
Pilon, M., Wienk, H., Sips, W., de Swaaf, M., Talboom, I., van 't Hof, R., de Korte-Kool, G., Demel, R., Weisbeek, P. and de Kruijff, B. 1995. J. Biol. Chem. 270: 3882-3893.
Quatroccio et al., Plant Mol. Biol. 15 (1990), 81-93
Quirasco et al (Appl. Environ. Microbiol., 65 (12), 5504-5509, 1999
Ritala et al., Plant Mol. Biol. 24, (1994), 317-325;
Ritchie et al, Transgenic Res. 2, (1993), 252-265).
Robyt, J. F. and Walseth, T. F. 1978. Carbohydr. Res. 61: 433-445.
Robyt, J. F. 1995. Adv. Carbohydr. Chem. Biochem. 51: 133-168.
Rocha-Sosa et al., EMBO J. 8, (1989), 29-33
Ruf S., Hermann M., Berger I. J., Carrer H., and Bock R. (2001). Nat. Biotechnol. 19 (9):870-875.
Sambrook et al., 2001. Molecular Cloning, A laboratory Manual, 3rd edition—Cold Spring Harbour Laboratory Press, Cold Spring Harbour, N.Y. ISBN:0879695773.
Shewmaker C K, Boyer C D, Wiesenborn D P, Thompson D B, Boersig M R, Oakes J V, Stalker D M. Plant Physiol. 1994 April; 104(4):1159-66.
Sidebotham, R. L. 1975. Adv. Carbohydr. Chem. Biochem. 30: 371-444.
Sidorov V. A., Kasten D., Pang S. Z., Hajdukiewicz P. T., Staub J. M., and Nehra N. S. (1999). Plant J. 19(2):209-216.
Sikdar S. R., et al. (1998). Plant Cell Reports 18:20-24.
Smeekens, S., van Binsbergen, J. and Weisbeek, P. 1985. Nucleic Acids Res. 13: 3179-3194
Spencer et al., Theor. Appl. Genet. 79, (1990), 625-631)
Staub et al. 1992 Plant Cell 4:39-45
Staub J. M., and Maliga P. (1993). EMBO J. 12 (2): 601-606.
Stockhaus et al., Proc. Natl. Acad. Sci. USA 84 (1987), 7943-7947
Stockhaus et al., EMBO J. 8 (1989), 2445-2451
Su D. and Robyt J F., Arch Biochem Biophys. 1994 Feb. 1; 308(2):471-6.
Sutherland, 2001
Svab Z., Hajdukiewicz P., and Maliga P. (1990). Proc. Natl. Acad. Sci. USA 87 (21):8526-8530.
Svab Z., Maliga P. (1993); Proc. Natl. Acad. Sci. USA February 1; 90(3):913-7.
Takken, F. L. W., Luderer, R., Gabriëls, S. H. E. J., Westerink, N., Lu, R., de Wit, P. J. G. M. and Joosten, M. H. A. J. 2000. Plant J. 24: 275-283.
Thompson et al., Nucleic Acids Research 22 (1994), 4673-4680
Tomás-Barberán and Espin, 2001
Van Geel-Schutten G H, Faber E J, Smit E, Bonting K, Smith M R, Ten Brink B, Kamerling J P, Vliegenthart J F, Dijkhuizen L., Appl Environ Microbiol. 1999 July; 65(7):3008-14.
Vasil et al., Bio/Technology 11 (1993), 1553-1558;
Wan and Lemaux, Plant Physiol. 104, (1994), 37-48
Wang, D., Liu, S., Trummer, B. J., Deng, C. and Wang, A. 2002. Nature Biotechnol. 20: 275-281.
Weising K, Schell J, Kahl G., Annu Rev Genet. 1988; 22:421-77. Review
Wenzler, H. C., Mignery, A., Fisher, L. M. and Park, W. D. 1989. Plant Mol. Biol. 12: 41-50.
Werr et al., EMBO J. 4 (1985), 1373-1380
Wiater A, Choma A, Szczodrak J, 1999, J. Basic Microbiol. 39, 265-273.
Wiater A and Szczodrak J, 2002, Acta Biol. Hung. 53, 389-401.
Wilmink et al., Plant Cell Reports 11, (1992), 76-80;
White et al., Nucleic Acid Res. 18(4):1062.
Wolter et al, Proc. Natl. Acad. Sci. USA 85 (1988), 846-850
Yoshihara et al., FEBS Lett. 383 (1996), 213-218
Zheng et al., Plant J. 4 (1993), 357-366

The invention claimed is:

1. A genetically modified plant cell comprising an enzymatic activity of a mutansucrase protein in their plastids and wherein said genetically modified plant cell synthesizes a modified starch in comparison to starch synthesized by corresponding non-genetically modified wild-type plant cells, wherein said plant cell comprises a nucleic acid molecule encoding a mutansucrase protein comprising:
   a) a nucleic acid molecule encoding the protein of SEQ ID NO: 2 or parts thereof;
   b) a nucleic acid molecule encoding a protein having at least 95% sequence identity to SEQ ID NO: 2 or parts thereof;
   c) a nucleic acid molecule comprising the nucleotide sequence of SEQ NO: 1, or parts thereof;
   d) a nucleic acid molecule having at least 95% identity to nucleic acids 439-3153 of SEQ ID NO: 1; or
   e) a nucleic acid molecule that deviates from the nucleic acid molecules of a), b), c), or d) due to the degeneration of the genetic code;
   wherein said nucleic acid molecules or parts thereof encode a mutansucrase protein capable of catalyzing the synthesis of mutan from sucrose; and wherein the nucleic acid molecule or parts thereof encoding a mutansucrase protein is stably integrated into the genome of the plant cell.

2. The genetically modified plant cell of claim 1, wherein the plant cell synthesizes a modified starch which has an increased T-onset temperature, an increased minimum viscosity, an increased end viscosity, increased gel strength, and/or an altered granule morphology in comparison to starch synthesized by corresponding non-genetically modified wild-type plant cells.

3. A plant and/or progeny thereof comprising the genetically modified plant cell of claim 1, wherein said plant comprises a nucleic acid molecule encoding a mutansucrase protein comprising:
   a) a nucleic acid molecule encoding the protein of SEQ ID NO: 2 or parts thereof;
   b) a nucleic acid molecule encoding a protein having at least 95% sequence identity to SEQ ID NO: 2 or parts thereof;
   c) a nucleic acid molecule comprising the nucleotide sequence of SEQ NO: 1, or parts thereof;
   d) a nucleic acid molecule having at least 95% identity to nucleic acids 439-3153 of SEQ ID NO: 1; or
   e) a nucleic acid molecule that deviates from the nucleic acid molecules of a), b), c), or d) due to the degeneration of the genetic code;
   wherein said nucleic acid molecules or parts thereof encode a mutansucrase protein capable of catalyzing the synthesis of mutan from sucrose.

4. The plant and/or progeny thereof of claim 3, wherein said plant and/or progeny thereof is a starch-storing plant.

5. The plant and/or progeny thereof of claim 4, wherein said plant and/or progeny thereof is a potato plant.

6. Propagation material of the plant of claim 3.

7. Harvestable parts of the plant of claim 3.

8. A method for the manufacture of the genetically modified plant of claim 3, said method comprising
   i) transforming a plant cell with a nucleic acid molecule comprising a nucleic acid molecule encoding a mutansucrase protein,
   ii) regenerating a plant from a plant cell obtained in step i), and
   iii) optionally, producing further plants from the plants obtained in step ii). wherein the nucleic acid molecule encoding a mutansucrase protein comprises:
      a) a nucleic acid molecule encoding the protein of SEQ ID NO: 2 or parts thereof;
      b) a nucleic acid molecule encoding a protein having at least 95% sequence identity to SEQ ID NO: 2 or parts thereof;
      c) a nucleic acid molecule comprising the nucleotide sequence of SEQ NO: 1, or parts thereof;
      d) a nucleic acid molecule having at least 95% identity to nucleic acids 439-3153 of SEQ ID NO: 1; or
      e) a nucleic acid molecule that deviates from the nucleic acid molecules of a), b), c), or d) due to the degeneration of the genetic code;
   wherein said nucleic acid molecules or parts thereof encode a mutansucrase protein capable of catalyzing the synthesis of mutan from sucrose.

9. The method of claim 8, wherein the nucleic acid molecule encoding the mutansucrase protein in step a) is translationally fused with a nucleic acid molecule encoding a plastidial signal sequence.

10. The method of claim 8, wherein the nucleic acid molecule encoding the mutansucrase protein is integrated into the plastidial genome of the plant.

11. A method for the manufacture of a modified starch comprising the step of extracting the starch from the plant cell of claim 1.

12. A method for the manufacture of a modified starch comprising the step of extracting the starch from the plant and/or progeny thereof of claim 3.

13. A method for producing a derived starch, said method comprising isolating starch from the plant cell of claim 1, and subjecting the starch to a temperature treatment or acid treatment, and wherein the starch is a starch ether, cross-linked starch, a graft polymer, an oxidized starch or a starch ether.

14. A method for producing a derived starch, said method comprising isolating starch from the plant and/or progeny thereof of claim 3, and subjecting the starch to a temperature treatment or acid treatment, and wherein the starch is a starch ether, cross-linked starch, a graft polymer, an oxidized starch or a starch ether.

15. Propagation material of the plant of claim 4.

16. Harvestable parts of the plant of claim 4.

17. Propagation material of the plant of claim 5.

18. Harvestable parts of the plant of claim 5.

19. The genetically modified plant cell of claim 1, wherein the mutansucrase protein is a truncated mutansucrase protein and wherein the C-terminal glucan-binding domain is deleted.

20. The genetically modified plant cell of claim 19, wherein said truncated mutansucrase protein catalyzes the synthesis of mutan from sucrose and is encoded by a nucleic acid molecule comprising:
   a) a nucleic acid molecule encoding a protein of SEQ ID NO: 4;
   b) a nucleic acid molecule encoding a protein having at least 95% identity to SEQ ID NO: 4 or parts thereof, having the capability of catalyzing the synthesis of mutan from sucrose, wherein the parts thereof encode proteins having at least 95% identity to SEQ ID NO: 4 from position 109 to 1012;
   c) a nucleic acid molecule encoding an amino acid sequence of an active core region of the mutansucrase protein, and optionally also a truncated variable region of a mutansucrase protein;

d) a nucleic acid molecule comprising the nucleotide sequence of SEQ ID NO: 3;

e) a nucleic acid molecule having at least 95% identity to position 325 to 3036 of SEQ ID 3; or f) a nucleic acid molecule that deviates from the nucleic acid sequence of d) or e) due to the degeneration of the genetic code;

wherein said plant cell comprises enzymatic activity of a catalytically active truncated mutansucrase.

21. The method of claim 8, wherein the mutansucrase protein is a truncated mutansucrase protein and wherein the C-terminal glucan-binding domain is deleted.

22. The method of claim 8, wherein the truncated mutansucrase protein that catalyzes the synthesis of mutan from sucrose and is encoded by a nucleic acid molecule comprising:

a) a nucleic acid molecule encoding a protein of SEQ ID NO: 4;

b) a nucleic acid molecule encoding a protein having at least 95% identity to SEQ ID NO: 4 or parts thereof, having the capability of catalyzing the synthesis of mutan from sucrose, wherein the parts thereof encode proteins having at least 95% identity to SEQ ID NO: 4 from position 109 to 1012;

c) a nucleic acid molecule encoding an amino acid sequence of an active core region of the mutansucrase protein, and optionally also a truncated variable region of a mutansucrase protein;

d) a nucleic acid molecule comprising the nucleotide sequence of SEQ ID NO: 3;

e) a nucleic acid molecule having at least 95% identity to position 325 to 3036 of SEQ ID 3; or f) a nucleic acid molecule that deviates from the nucleic acid sequence of d) or e) due to the degeneration of the genetic code;

wherein said plant cell comprises enzymatic activity of a catalytically active truncated mutansucrase.

23. The method of claim 1, wherein the parts thereof encodes a protein having at least 95% identity to SEQ ID NO: 4 from position 109 to 1012.

24. New The method of claim 8, wherein the parts thereof encodes a protein having at least 95% identity to SEQ ID NO: 4 from position 109 to 1012.

* * * * *

SEQUENCE LISTING

```
<160> NUMBER OF SEQ ID NOS: 12

<210> SEQ ID NO 1
<211> LENGTH: 4794
<212> TYPE: DNA
<213> ORGANISM: Streptococcus downei
<220> FEATURE:
<221> NAME/KEY: sig_peptide
<222> LOCATION: (1)..(114)
<223> OTHER INFORMATION: sequence encoding mutansucrase signal peptide
```

```
                                    for secretion
<220> FEATURE:
<221> NAME/KEY: CDS
<222> LOCATION: (1)..(4791)
<223> OTHER INFORMATION: coding sequence
<220> FEATURE:
<221> NAME/KEY: misc_feature
<222> LOCATION: (3154)..(4197)
<223> OTHER INFORMATION: C-terminal (glucan binding) domain of gene
      encoding mutansucrase
<220> FEATURE:
<221> NAME/KEY: misc_feature
<222> LOCATION: (115)..(438)
<223> OTHER INFORMATION: variable region of gene encoding mutansucrase
<220> FEATURE:
<221> NAME/KEY: misc_feature
<222> LOCATION: (439)..(3153)
<223> OTHER INFORMATION: active core region of gene encoding
      mutansucrase

<400> SEQUENCE: 1 atg gag aag aat gaa cgt ttt aag atg cat aag gtc aaa aag aga tgg        48
Met Glu Lys Asn Glu Arg Phe Lys Met His Lys Val Lys Lys Arg Trp
1               5                   10                  15 gtg act atc tca gtt gca tct gcc act atg tta gct tca gct ctc ggt        96
Val Thr Ile Ser Val Ala Ser Ala Thr Met Leu Ala Ser Ala Leu Gly
            20                  25                  30 gct tca gtt gct agc gca gat act gaa act gtt agc gaa gac agc aac       144
Ala Ser Val Ala Ser Ala Asp Thr Glu Thr Val Ser Glu Asp Ser Asn
        35                  40                  45 caa gca gtc ttg acg gct gac caa acg act acc aac caa gat act gag       192
Gln Ala Val Leu Thr Ala Asp Gln Thr Thr Thr Asn Gln Asp Thr Glu
    50                  55                  60 caa act tct gtt gca gcg aca gct aca tca gaa cag tct gct tca act       240
Gln Thr Ser Val Ala Ala Thr Ala Thr Ser Glu Gln Ser Ala Ser Thr
65                  70                  75                  80 gat gca gca aca gat caa gca tca gca aca gat caa gca tca gca gca       288
Asp Ala Ala Thr Asp Gln Ala Ser Ala Thr Asp Gln Ala Ser Ala Ala
                85                  90                  95 gag caa act caa gga aca aca gct agc aca gac acg gca gct caa aca       336
Glu Gln Thr Gln Gly Thr Thr Ala Ser Thr Asp Thr Ala Ala Gln Thr
            100                 105                 110 acc aca aat gct aat gaa gct aag tgg gtt ccg act gaa aat gag aac       384
Thr Thr Asn Ala Asn Glu Ala Lys Trp Val Pro Thr Glu Asn Glu Asn
        115                 120                 125 caa gtt ttt aca gat gag atg tta gca gaa gcc aag aat gtg gct act       432
Gln Val Phe Thr Asp Glu Met Leu Ala Glu Ala Lys Asn Val Ala Thr
    130                 135                 140 gct gaa tct aat tca att cca tca gac ttg gct aaa atg tca aat gtt       480
Ala Glu Ser Asn Ser Ile Pro Ser Asp Leu Ala Lys Met Ser Asn Val
145                 150                 155                 160 aag cag gtt gac ggt aaa tat tat tac tac gat caa gac ggc aac gtt       528
Lys Gln Val Asp Gly Lys Tyr Tyr Tyr Tyr Asp Gln Asp Gly Asn Val
                165                 170                 175 aag aag aac ttt gct gtt agc gtt ggt gag aag atc tat tac ttt gat       576
Lys Lys Asn Phe Ala Val Ser Val Gly Glu Lys Ile Tyr Tyr Phe Asp
            180                 185                 190 gaa act ggc gct tac aaa gac act agc aag gta gaa gcg gat aaa tca       624
Glu Thr Gly Ala Tyr Lys Asp Thr Ser Lys Val Glu Ala Asp Lys Ser
        195                 200                 205 ggt tct gat atc agc aaa gaa gaa aca acc ttt gct gct aac aac cgt       672
Gly Ser Asp Ile Ser Lys Glu Glu Thr Thr Phe Ala Ala Asn Asn Arg
    210                 215                 220 gct tac agt acc tca gct gaa aac ttt gaa gcc att gat aac tac ttg       720
Ala Tyr Ser Thr Ser Ala Glu Asn Phe Glu Ala Ile Asp Asn Tyr Leu
```

-continued

```
              225                 230                 235                 240
aca gct gac tca tgg tac cgt cca aag tct atc ctc aag gat ggt aag        768
Thr Ala Asp Ser Trp Tyr Arg Pro Lys Ser Ile Leu Lys Asp Gly Lys
                    245                 250                 255 act tgg aca gaa tca agc aag gat gac ttc cgt ccg cta ttg atg gct        816
Thr Trp Thr Glu Ser Ser Lys Asp Asp Phe Arg Pro Leu Leu Met Ala
            260                 265                 270 tgg tgg cca gat acc gaa acc aaa cgc aac tat gtt aac tac atg aac        864
Trp Trp Pro Asp Thr Glu Thr Lys Arg Asn Tyr Val Asn Tyr Met Asn
        275                 280                 285 aag gtt gtt ggt atc gat aaa acc tat acc gct gaa aca agc cag gct        912
Lys Val Val Gly Ile Asp Lys Thr Tyr Thr Ala Glu Thr Ser Gln Ala
    290                 295                 300 gac ctg aca gca gca gct gaa ctg gtt caa gcc cgt atc gaa caa aag        960
Asp Leu Thr Ala Ala Ala Glu Leu Val Gln Ala Arg Ile Glu Gln Lys
305                 310                 315                 320 att aca act gaa caa aat acc aaa tgg ttg cgt gaa gct atc tca gct       1008
Ile Thr Thr Glu Gln Asn Thr Lys Trp Leu Arg Glu Ala Ile Ser Ala
                    325                 330                 335 ttt gtt aaa act caa cca caa tgg aat ggt gaa agc gaa aag cca tac       1056
Phe Val Lys Thr Gln Pro Gln Trp Asn Gly Glu Ser Glu Lys Pro Tyr
            340                 345                 350 gat gac cac ttg caa aat ggt gcc ctc aag ttc gat aac caa tct gat       1104
Asp Asp His Leu Gln Asn Gly Ala Leu Lys Phe Asp Asn Gln Ser Asp
        355                 360                 365 ttg aca cca gat acg caa tcg aac tat cgt ttg ctc aat cgc aca cca       1152
Leu Thr Pro Asp Thr Gln Ser Asn Tyr Arg Leu Leu Asn Arg Thr Pro
    370                 375                 380 act aac caa act ggt tcc ctg gac tct cgt ttc acc tac aat gct aac       1200
Thr Asn Gln Thr Gly Ser Leu Asp Ser Arg Phe Thr Tyr Asn Ala Asn
385                 390                 395                 400 gac ccg tta ggt ggt tat gag ttg ctt ctg gct aac gac gtg gat aac       1248
Asp Pro Leu Gly Gly Tyr Glu Leu Leu Leu Ala Asn Asp Val Asp Asn
                    405                 410                 415 tct aat ccc atc gtt caa gca gag caa ctc aac tgg ctg cat tac ctg       1296
Ser Asn Pro Ile Val Gln Ala Glu Gln Leu Asn Trp Leu His Tyr Leu
            420                 425                 430 ctc aac ttc ggt act atc tat gct aaa gat gcg gat gct aac ttt gac       1344
Leu Asn Phe Gly Thr Ile Tyr Ala Lys Asp Ala Asp Ala Asn Phe Asp
        435                 440                 445 tct atc cgt gtt gat gcg gta gat aat gtc gat gct gac ctt ctg caa       1392
Ser Ile Arg Val Asp Ala Val Asp Asn Val Asp Ala Asp Leu Leu Gln
    450                 455                 460 atc tct agt gat tac ctt aag gca gct tac ggt atc gat aaa aac aac       1440
Ile Ser Ser Asp Tyr Leu Lys Ala Ala Tyr Gly Ile Asp Lys Asn Asn
465                 470                 475                 480 aaa aat gct aat aac cac gtt tct atc gta gaa gca tgg agc gac aac       1488
Lys Asn Ala Asn Asn His Val Ser Ile Val Glu Ala Trp Ser Asp Asn
                    485                 490                 495 gat acc cct tat ctc cat gat gat ggc gac aac ctc atg aac atg gac       1536
Asp Thr Pro Tyr Leu His Asp Asp Gly Asp Asn Leu Met Asn Met Asp
            500                 505                 510 aac aag ttc cgt ttg tct atg ctt tgg tct ttg gct aaa cca ttg gac       1584
Asn Lys Phe Arg Leu Ser Met Leu Trp Ser Leu Ala Lys Pro Leu Asp
        515                 520                 525 aaa cgt tct ggc ttg aat ccc ctc atc cac aac agt ctg gtt gac cgt       1632
Lys Arg Ser Gly Leu Asn Pro Leu Ile His Asn Ser Leu Val Asp Arg
    530                 535                 540 gaa gtg gat gac cgt gaa gtt gaa acc gtt cca agt tac agc ttt gcc       1680
Glu Val Asp Asp Arg Glu Val Glu Thr Val Pro Ser Tyr Ser Phe Ala
```

-continued

```
         545                 550                 555                 560 cgt gct cac gat agc gaa gta caa gac ctg att cgt gac atc atc aag    1728
Arg Ala His Asp Ser Glu Val Gln Asp Leu Ile Arg Asp Ile Ile Lys
            565                 570                 575 gct gaa att aat cca aat gca ttt ggt tat tca ttt act caa gac gaa    1776
Ala Glu Ile Asn Pro Asn Ala Phe Gly Tyr Ser Phe Thr Gln Asp Glu
                580                 585                 590 atc gac caa gcc ttc aag att tac aac gaa gac ctc aag aag acc gat    1824
Ile Asp Gln Ala Phe Lys Ile Tyr Asn Glu Asp Leu Lys Lys Thr Asp
            595                 600                 605 aag aaa tac act cac tac aat gtg ccg ctt tct tat acc ttg ctt ctg    1872
Lys Lys Tyr Thr His Tyr Asn Val Pro Leu Ser Tyr Thr Leu Leu Leu
        610                 615                 620 act aac aag ggt tcg att cct cgc gtc tat tat gga gat atg ttc acc    1920
Thr Asn Lys Gly Ser Ile Pro Arg Val Tyr Tyr Gly Asp Met Phe Thr
625                 630                 635                 640 gat gat ggt caa tac atg gcc aac aag act gtg aac tac gat gct atc    1968
Asp Asp Gly Gln Tyr Met Ala Asn Lys Thr Val Asn Tyr Asp Ala Ile
            645                 650                 655 gaa tct ctg ctg aaa gcc cgt atg aag tac gtt gct ggt ggt caa gct    2016
Glu Ser Leu Leu Lys Ala Arg Met Lys Tyr Val Ala Gly Gly Gln Ala
                660                 665                 670 atg caa aat tac caa atc ggt aat ggc gaa atc ttg act tct gtc cgt    2064
Met Gln Asn Tyr Gln Ile Gly Asn Gly Glu Ile Leu Thr Ser Val Arg
            675                 680                 685 tat ggt aag ggt gcc ctt aaa caa agc gat aag ggt gat gcg aca act    2112
Tyr Gly Lys Gly Ala Leu Lys Gln Ser Asp Lys Gly Asp Ala Thr Thr
        690                 695                 700 cgt acg tca ggt gtc ggc gtt gtt atg gga aac caa ccc aac ttt agc    2160
Arg Thr Ser Gly Val Gly Val Val Met Gly Asn Gln Pro Asn Phe Ser
705                 710                 715                 720 ttg gat gga aag gtt gta gcc ctc aac atg ggt gct gcc cac gct aac    2208
Leu Asp Gly Lys Val Val Ala Leu Asn Met Gly Ala Ala His Ala Asn
                725                 730                 735 caa gaa tac cgt gct ctt atg gta tca act aaa gac ggt gtt gca acc    2256
Gln Glu Tyr Arg Ala Leu Met Val Ser Thr Lys Asp Gly Val Ala Thr
            740                 745                 750 tat gct aca gat gct gat gct agc aag gct ggt ctg gtt aag cgc aca    2304
Tyr Ala Thr Asp Ala Asp Ala Ser Lys Ala Gly Leu Val Lys Arg Thr
        755                 760                 765 gat gaa aat ggt tac ctc tac ttc ttg aac gac gat ctc aag ggg gtt    2352
Asp Glu Asn Gly Tyr Leu Tyr Phe Leu Asn Asp Asp Leu Lys Gly Val
    770                 775                 780 gct aac cct cag gtt tct ggt ttc ctt caa gtc tgg gta cca gtg gga    2400
Ala Asn Pro Gln Val Ser Gly Phe Leu Gln Val Trp Val Pro Val Gly
785                 790                 795                 800 gca gca gat gac caa gat att cgt gta gca gct agc gat aca gca agt    2448
Ala Ala Asp Asp Gln Asp Ile Arg Val Ala Ala Ser Asp Thr Ala Ser
                805                 810                 815 acc gat gga aaa tca ctc cat caa gat gct gcc atg gac tct cgc gtc    2496
Thr Asp Gly Lys Ser Leu His Gln Asp Ala Ala Met Asp Ser Arg Val
            820                 825                 830 atg ttt gaa ggt ttc tct aac ttc caa tct ttt gcg aca aaa gaa gaa    2544
Met Phe Glu Gly Phe Ser Asn Phe Gln Ser Phe Ala Thr Lys Glu Glu
        835                 840                 845 gag tat acc aat gtt gtt att gct aac aat gtt gat aaa ttt gtt tca    2592
Glu Tyr Thr Asn Val Val Ile Ala Asn Asn Val Asp Lys Phe Val Ser
    850                 855                 860 tgg gga atc act gac ttt gaa atg gct cct cag tat gtc tca tct act    2640
Trp Gly Ile Thr Asp Phe Glu Met Ala Pro Gln Tyr Val Ser Ser Thr
```

-continued

```
            865                 870                 875                 880
gac ggt cag ttc ctt gat tct gtc att caa aat ggt tat gcc ttt acc          2688
Asp Gly Gln Phe Leu Asp Ser Val Ile Gln Asn Gly Tyr Ala Phe Thr
                    885                 890                 895 gac cgt tat gac ttg ggt atg tct aaa gca aac aag tat ggt aca gcc          2736
Asp Arg Tyr Asp Leu Gly Met Ser Lys Ala Asn Lys Tyr Gly Thr Ala
                900                 905                 910 gac caa ttg gtt aag gct atc aag gct ctc cat gct aaa ggc ctg aag          2784
Asp Gln Leu Val Lys Ala Ile Lys Ala Leu His Ala Lys Gly Leu Lys
            915                 920                 925 gtt atg gca gac tgg gtt cca gac caa atg tac acc ttc cct aaa caa          2832
Val Met Ala Asp Trp Val Pro Asp Gln Met Tyr Thr Phe Pro Lys Gln
        930                 935                 940 gaa gtg gtc act gtt act cgg aca gat aag ttt ggc aaa cca atc gca          2880
Glu Val Val Thr Val Thr Arg Thr Asp Lys Phe Gly Lys Pro Ile Ala
945                 950                 955                 960 gga agc caa att aat cac agt ctc tac gta aca gat aca aag agc tct          2928
Gly Ser Gln Ile Asn His Ser Leu Tyr Val Thr Asp Thr Lys Ser Ser
                965                 970                 975 ggt gat gac tat caa gct aaa tac ggc ggt gcc ttc ctt gac gaa tta          2976
Gly Asp Asp Tyr Gln Ala Lys Tyr Gly Gly Ala Phe Leu Asp Glu Leu
            980                 985                 990 aag gaa aaa tat cca gaa ctc ttt  acc aag aag caa atc  tct acc ggc        3024
Lys Glu Lys Tyr Pro Glu Leu Phe  Thr Lys Lys Gln Ile  Ser Thr Gly
                995                 1000                1005 caa gcc  ata gat cca tct gtt  aag att aaa caa tgg  tct gct aag           3069
Gln Ala  Ile Asp Pro Ser Val  Lys Ile Lys Gln Trp  Ser Ala Lys
     1010                1015                1020 tac ttc  aac ggt agc aat atc  ctt ggc cgg ggt gcc  gat tat gtc           3114
Tyr Phe  Asn Gly Ser Asn Ile  Leu Gly Arg Gly Ala  Asp Tyr Val
     1025                1030                1035 ctc agc  gac caa gca agc aac  aag tac ctc aat gtt  tca gat gat           3159
Leu Ser  Asp Gln Ala Ser Asn  Lys Tyr Leu Asn Val  Ser Asp Asp
     1040                1045                1050 aaa ctc  ttc ttg cca aaa act  ctc cta ggt caa gtc  gta gaa tca           3204
Lys Leu  Phe Leu Pro Lys Thr  Leu Leu Gly Gln Val  Val Glu Ser
     1055                1060                1065 ggt atc  cgc ttt gat gga act  ggt tat gtc tac aac  tca agc aca           3249
Gly Ile  Arg Phe Asp Gly Thr  Gly Tyr Val Tyr Asn  Ser Ser Thr
     1070                1075                1080 aca ggt  gaa aag gta acc gat  agc ttt att act gaa  gct ggt aat           3294
Thr Gly  Glu Lys Val Thr Asp  Ser Phe Ile Thr Glu  Ala Gly Asn
     1085                1090                1095 ctt tac  tac ttt ggc caa gat  ggt tac atg gtg act  ggt gcc caa           3339
Leu Tyr  Tyr Phe Gly Gln Asp  Gly Tyr Met Val Thr  Gly Ala Gln
     1100                1105                1110 aac atc  aag gga tct aac tat  tac ttc ctg gct aat  ggt gct gcc           3384
Asn Ile  Lys Gly Ser Asn Tyr  Tyr Phe Leu Ala Asn  Gly Ala Ala
     1115                1120                1125 ctt cgc  aat aca gtt tat act  gat gcc caa ggt caa  aac cat tac           3429
Leu Arg  Asn Thr Val Tyr Thr  Asp Ala Gln Gly Gln  Asn His Tyr
     1130                1135                1140 tat ggc  aac gac ggt aaa cgt  tac gaa aat ggt tac  caa caa ttt           3474
Tyr Gly  Asn Asp Gly Lys Arg  Tyr Glu Asn Gly Tyr  Gln Gln Phe
     1145                1150                1155 ggt aat  gac agc tgg cgt tac  ttc aag aat ggt gtc  atg gca ctt           3519
Gly Asn  Asp Ser Trp Arg Tyr  Phe Lys Asn Gly Val  Met Ala Leu
     1160                1165                1170 ggc ctg  aca acc gtt gat ggt  cac gtt caa tac ttt  gat aaa gat           3564
Gly Leu  Thr Thr Val Asp Gly  His Val Gln Tyr Phe  Asp Lys Asp
```

-continued

| | | |
|---|---|---|
| 1175 | 1180 | 1185 |

| | |
|---|---|
| ggt gtt caa gct aag gat aag att att gtc acc cgt gat ggt aag<br>Gly Val Gln Ala Lys Asp Lys Ile Ile Val Thr Arg Asp Gly Lys<br>1190                     1195                     1200 | 3609 |
| gtt cgt tac ttc gac caa cat aat gga aat gct gta acc aat acc<br>Val Arg Tyr Phe Asp Gln His Asn Gly Asn Ala Val Thr Asn Thr<br>1205                     1210                     1215 | 3654 |
| ttc gtc gct gac aag act ggt cac tgg tac tat cta ggt aaa gat<br>Phe Val Ala Asp Lys Thr Gly His Trp Tyr Tyr Leu Gly Lys Asp<br>1220                     1225                     1230 | 3699 |
| ggt gtc gct gtt acc ggt gct caa act gtt ggt aaa caa cac ctt<br>Gly Val Ala Val Thr Gly Ala Gln Thr Val Gly Lys Gln His Leu<br>1235                     1240                     1245 | 3744 |
| tac ttc gaa gcc aat ggt caa caa gtt aag ggt gac ttt gtc aca<br>Tyr Phe Glu Ala Asn Gly Gln Gln Val Lys Gly Asp Phe Val Thr<br>1250                     1255                     1260 | 3789 |
| gcc aaa gat ggt aaa ctt tac ttc tac gat gtt gac tct ggt gac<br>Ala Lys Asp Gly Lys Leu Tyr Phe Tyr Asp Val Asp Ser Gly Asp<br>1265                     1270                     1275 | 3834 |
| atg tgg acc aat acc ttc att gaa gac aag gca ggc aac tgg ttc<br>Met Trp Thr Asn Thr Phe Ile Glu Asp Lys Ala Gly Asn Trp Phe<br>1280                     1285                     1290 | 3879 |
| tat ctt ggt aaa gat ggc gca gct gtc aca ggt gct caa acc atc<br>Tyr Leu Gly Lys Asp Gly Ala Ala Val Thr Gly Ala Gln Thr Ile<br>1295                     1300                     1305 | 3924 |
| aag ggc caa aaa ctt tac ttc aag gct aac ggc caa caa gtt aag<br>Lys Gly Gln Lys Leu Tyr Phe Lys Ala Asn Gly Gln Gln Val Lys<br>1310                     1315                     1320 | 3969 |
| ggt gat atc gtc aag gat gcc gat ggt aag att cgt tac tac gat<br>Gly Asp Ile Val Lys Asp Ala Asp Gly Lys Ile Arg Tyr Tyr Asp<br>1325                     1330                     1335 | 4014 |
| gcc caa act ggt gaa caa gtc ttt aat aag tct gta agt gtt aac<br>Ala Gln Thr Gly Glu Gln Val Phe Asn Lys Ser Val Ser Val Asn<br>1340                     1345                     1350 | 4059 |
| ggt aag act tac tac ttc ggt agt gat gga act gct caa act cag<br>Gly Lys Thr Tyr Tyr Phe Gly Ser Asp Gly Thr Ala Gln Thr Gln<br>1355                     1360                     1365 | 4104 |
| gct aat cca aag ggt caa acc ttt aag gat ggt tct gga gtt ctt<br>Ala Asn Pro Lys Gly Gln Thr Phe Lys Asp Gly Ser Gly Val Leu<br>1370                     1375                     1380 | 4149 |
| cgt ttc tac aat ctt gaa ggt cag tat gta tca ggt agt gga tgg<br>Arg Phe Tyr Asn Leu Glu Gly Gln Tyr Val Ser Gly Ser Gly Trp<br>1385                     1390                     1395 | 4194 |
| tat gaa aca gca gag cac gaa tgg gtt tat gtt aaa tct ggt aag<br>Tyr Glu Thr Ala Glu His Glu Trp Val Tyr Val Lys Ser Gly Lys<br>1400                     1405                     1410 | 4239 |
| gta ttg act ggt gct caa acc att gga aat caa cga gtt tac ttc<br>Val Leu Thr Gly Ala Gln Thr Ile Gly Asn Gln Arg Val Tyr Phe<br>1415                     1420                     1425 | 4284 |
| aag gat aat ggc cat caa gtc aaa ggt caa ttg gta act ggt aac<br>Lys Asp Asn Gly His Gln Val Lys Gly Gln Leu Val Thr Gly Asn<br>1430                     1435                     1440 | 4329 |
| gat ggt aag ctt cgc tac tat gat gcc aac tct ggc gac cag gct<br>Asp Gly Lys Leu Arg Tyr Tyr Asp Ala Asn Ser Gly Asp Gln Ala<br>1445                     1450                     1455 | 4374 |
| ttc aac aag tct gtg act gtt aat ggc aaa act tac tac ttc ggt<br>Phe Asn Lys Ser Val Thr Val Asn Gly Lys Thr Tyr Tyr Phe Gly<br>1460                     1465                     1470 | 4419 |
| agt gat gga act gct caa act cag gct aat cca aag ggt caa acc<br>Ser Asp Gly Thr Ala Gln Thr Gln Ala Asn Pro Lys Gly Gln Thr | 4464 |

-continued

```
                 1475                1480                1485
ttt aag gat ggt tct gga gtt ctt cgt ttc tac aat ctt gaa ggt      4509
Phe Lys Asp Gly Ser Gly Val Leu Arg Phe Tyr Asn Leu Glu Gly
    1490                1495                1500 cag tat gta tca ggt agt gga tgg tat aaa aat gcc caa ggt caa      4554
Gln Tyr Val Ser Gly Ser Gly Trp Tyr Lys Asn Ala Gln Gly Gln
1505                1510                1515 tgg ctt tac gtt aaa gac gga aaa gta ttg act ggc ctg cag aca      4599
Trp Leu Tyr Val Lys Asp Gly Lys Val Leu Thr Gly Leu Gln Thr
    1520                1525                1530 gta ggt aac caa aag gtt tac ttt gat aaa aat ggt atc caa gcc      4644
Val Gly Asn Gln Lys Val Tyr Phe Asp Lys Asn Gly Ile Gln Ala
    1535                1540                1545 aaa ggt aag gct gta aga act tct gat ggt aag gtt cgc tac ttt      4689
Lys Gly Lys Ala Val Arg Thr Ser Asp Gly Lys Val Arg Tyr Phe
    1550                1555                1560 gat gaa aat tct ggt agc atg att acc aac caa tgg aaa ttt gtt      4734
Asp Glu Asn Ser Gly Ser Met Ile Thr Asn Gln Trp Lys Phe Val
    1565                1570                1575 tac gga caa tat tac tat ttc ggt agt gat ggt gct gct gtc tac      4779
Tyr Gly Gln Tyr Tyr Tyr Phe Gly Ser Asp Gly Ala Ala Val Tyr
    1580                1585                1590 cgt ggc tgg aac taa                                              4794
Arg Gly Trp Asn
    1595

<210> SEQ ID NO 2
<211> LENGTH: 1597
<212> TYPE: PRT
<213> ORGANISM: Streptococcus downei
<220> FEATURE:
<221> NAME/KEY: misc_feature
<222> LOCATION: (3154)..(4197)
<223> OTHER INFORMATION: C-terminal (glucan binding) domain of gene
      encoding mutansucrase
<220> FEATURE:
<221> NAME/KEY: misc_feature
<222> LOCATION: (115)..(438)
<223> OTHER INFORMATION: variable region of gene encoding mutansucrase
<220> FEATURE:
<221> NAME/KEY: misc_feature
<222> LOCATION: (439)..(3153)
<223> OTHER INFORMATION: active core region of gene encoding
      mutansucrase

<400> SEQUENCE: 2

Met Glu Lys Asn Glu Arg Phe Lys Met His Lys Val Lys Lys Arg Trp
1               5                   10                  15

Val Thr Ile Ser Val Ala Ser Ala Thr Met Leu Ala Ser Ala Leu Gly
            20                  25                  30

Ala Ser Val Ala Ser Ala Asp Thr Glu Thr Val Ser Glu Asp Ser Asn
        35                  40                  45

Gln Ala Val Leu Thr Ala Asp Gln Thr Thr Asn Gln Asp Thr Glu
    50                  55                  60

Gln Thr Ser Val Ala Ala Thr Ala Thr Ser Glu Gln Ser Ala Ser Thr
65                  70                  75                  80

Asp Ala Ala Thr Asp Gln Ala Ser Ala Thr Asp Gln Ala Ser Ala Ala
                85                  90                  95

Glu Gln Thr Gln Gly Thr Thr Ala Ser Thr Asp Thr Ala Gln Thr
            100                 105                 110

Thr Thr Asn Ala Asn Glu Ala Lys Trp Val Pro Thr Glu Asn Glu Asn
        115                 120                 125
```

-continued

```
Gln Val Phe Thr Asp Glu Met Leu Ala Glu Ala Lys Asn Val Ala Thr
    130                 135                 140
Ala Glu Ser Asn Ser Ile Pro Ser Asp Leu Ala Lys Met Ser Asn Val
145                 150                 155                 160
Lys Gln Val Asp Gly Lys Tyr Tyr Tyr Asp Gln Asp Gly Asn Val
            165                 170                 175
Lys Lys Asn Phe Ala Val Ser Val Gly Glu Lys Ile Tyr Tyr Phe Asp
                180                 185                 190
Glu Thr Gly Ala Tyr Lys Asp Thr Ser Lys Val Glu Ala Asp Lys Ser
            195                 200                 205
Gly Ser Asp Ile Ser Lys Glu Thr Thr Phe Ala Ala Asn Asn Arg
210                 215                 220
Ala Tyr Ser Thr Ser Ala Glu Asn Phe Glu Ala Ile Asp Asn Tyr Leu
225                 230                 235                 240
Thr Ala Asp Ser Trp Tyr Arg Pro Lys Ser Ile Leu Lys Asp Gly Lys
                245                 250                 255
Thr Trp Thr Glu Ser Ser Lys Asp Asp Phe Arg Pro Leu Leu Met Ala
            260                 265                 270
Trp Trp Pro Asp Thr Glu Thr Lys Arg Asn Tyr Val Asn Tyr Met Asn
        275                 280                 285
Lys Val Val Gly Ile Asp Lys Thr Tyr Thr Ala Glu Thr Ser Gln Ala
    290                 295                 300
Asp Leu Thr Ala Ala Ala Glu Leu Val Gln Ala Arg Ile Glu Gln Lys
305                 310                 315                 320
Ile Thr Thr Glu Gln Asn Thr Lys Trp Leu Arg Glu Ala Ile Ser Ala
                325                 330                 335
Phe Val Lys Thr Gln Pro Gln Trp Asn Gly Glu Ser Glu Lys Pro Tyr
            340                 345                 350
Asp Asp His Leu Gln Asn Gly Ala Leu Lys Phe Asp Asn Gln Ser Asp
        355                 360                 365
Leu Thr Pro Asp Thr Gln Ser Asn Tyr Arg Leu Leu Asn Arg Thr Pro
    370                 375                 380
Thr Asn Gln Thr Gly Ser Leu Asp Ser Arg Phe Thr Tyr Asn Ala Asn
385                 390                 395                 400
Asp Pro Leu Gly Gly Tyr Glu Leu Leu Leu Ala Asn Asp Val Asp Asn
                405                 410                 415
Ser Asn Pro Ile Val Gln Ala Glu Gln Leu Asn Trp Leu His Tyr Leu
            420                 425                 430
Leu Asn Phe Gly Thr Ile Tyr Ala Lys Asp Ala Asp Ala Asn Phe Asp
        435                 440                 445
Ser Ile Arg Val Asp Ala Val Asp Asn Val Asp Ala Asp Leu Leu Gln
    450                 455                 460
Ile Ser Ser Asp Tyr Leu Lys Ala Ala Tyr Gly Ile Asp Lys Asn Asn
465                 470                 475                 480
Lys Asn Ala Asn Asn His Val Ser Ile Val Glu Ala Trp Ser Asp Asn
                485                 490                 495
Asp Thr Pro Tyr Leu His Asp Asp Gly Asp Asn Leu Met Asn Met Asp
            500                 505                 510
Asn Lys Phe Arg Leu Ser Met Leu Trp Ser Leu Ala Lys Pro Leu Asp
        515                 520                 525
Lys Arg Ser Gly Leu Asn Pro Leu Ile His Asn Ser Leu Val Asp Arg
    530                 535                 540
Glu Val Asp Asp Arg Glu Val Glu Thr Val Pro Ser Tyr Ser Phe Ala
545                 550                 555                 560
```

-continued

```
Arg Ala His Asp Ser Glu Val Gln Asp Leu Ile Arg Asp Ile Ile Lys
                565                 570                 575
Ala Glu Ile Asn Pro Asn Ala Phe Gly Tyr Ser Phe Thr Gln Asp Glu
            580                 585                 590
Ile Asp Gln Ala Phe Lys Ile Tyr Asn Glu Asp Leu Lys Lys Thr Asp
        595                 600                 605
Lys Lys Tyr Thr His Tyr Asn Val Pro Leu Ser Tyr Thr Leu Leu Leu
    610                 615                 620
Thr Asn Lys Gly Ser Ile Pro Arg Val Tyr Tyr Gly Asp Met Phe Thr
625                 630                 635                 640
Asp Asp Gly Gln Tyr Met Ala Asn Lys Thr Val Asn Tyr Asp Ala Ile
                645                 650                 655
Glu Ser Leu Leu Lys Ala Arg Met Lys Tyr Val Ala Gly Gly Gln Ala
            660                 665                 670
Met Gln Asn Tyr Gln Ile Gly Asn Gly Glu Ile Leu Thr Ser Val Arg
        675                 680                 685
Tyr Gly Lys Gly Ala Leu Lys Gln Ser Asp Lys Gly Asp Ala Thr Thr
    690                 695                 700
Arg Thr Ser Gly Val Gly Val Val Met Gly Asn Gln Pro Asn Phe Ser
705                 710                 715                 720
Leu Asp Gly Lys Val Val Ala Leu Asn Met Gly Ala Ala His Ala Asn
                725                 730                 735
Gln Glu Tyr Arg Ala Leu Met Val Ser Thr Lys Asp Gly Val Ala Thr
            740                 745                 750
Tyr Ala Thr Asp Ala Asp Ala Ser Lys Ala Gly Leu Val Lys Arg Thr
        755                 760                 765
Asp Glu Asn Gly Tyr Leu Tyr Phe Leu Asn Asp Asp Leu Lys Gly Val
    770                 775                 780
Ala Asn Pro Gln Val Ser Gly Phe Leu Gln Val Trp Val Pro Val Gly
785                 790                 795                 800
Ala Ala Asp Asp Gln Asp Ile Arg Val Ala Ala Ser Asp Thr Ala Ser
                805                 810                 815
Thr Asp Gly Lys Ser Leu His Gln Asp Ala Ala Met Asp Ser Arg Val
            820                 825                 830
Met Phe Glu Gly Phe Ser Asn Phe Gln Ser Phe Ala Thr Lys Glu Glu
        835                 840                 845
Glu Tyr Thr Asn Val Val Ile Ala Asn Asn Val Asp Lys Phe Val Ser
    850                 855                 860
Trp Gly Ile Thr Asp Phe Glu Met Ala Pro Gln Tyr Val Ser Ser Thr
865                 870                 875                 880
Asp Gly Gln Phe Leu Asp Ser Val Ile Gln Asn Gly Tyr Ala Phe Thr
                885                 890                 895
Asp Arg Tyr Asp Leu Gly Met Ser Lys Ala Asn Lys Tyr Gly Thr Ala
            900                 905                 910
Asp Gln Leu Val Lys Ala Ile Lys Ala Leu His Ala Lys Gly Leu Lys
        915                 920                 925
Val Met Ala Asp Trp Val Pro Asp Gln Met Tyr Thr Phe Pro Lys Gln
    930                 935                 940
Glu Val Val Thr Val Thr Arg Thr Asp Lys Phe Gly Lys Pro Ile Ala
945                 950                 955                 960
Gly Ser Gln Ile Asn His Ser Leu Tyr Val Thr Asp Thr Lys Ser Ser
                965                 970                 975
Gly Asp Asp Tyr Gln Ala Lys Tyr Gly Gly Ala Phe Leu Asp Glu Leu
```

-continued

```
                980                 985                 990
Lys Glu Lys Tyr Pro Glu Leu Phe  Thr Lys Lys Gln Ile  Ser Thr Gly
            995                 1000                1005

Gln Ala  Ile Asp Pro Ser Val  Lys Ile Lys Gln Trp  Ser Ala Lys
    1010                1015                1020

Tyr Phe  Asn Gly Ser Asn Ile  Leu Gly Arg Gly Ala  Asp Tyr Val
    1025                1030                1035

Leu Ser  Asp Gln Ala Ser Asn  Lys Tyr Leu Asn Val  Ser Asp Asp
    1040                1045                1050

Lys Leu  Phe Leu Pro Lys Thr  Leu Leu Gly Gln Val  Val Glu Ser
    1055                1060                1065

Gly Ile  Arg Phe Asp Gly Thr  Gly Tyr Val Tyr Asn  Ser Ser Thr
    1070                1075                1080

Thr Gly  Glu Lys Val Thr Asp  Ser Phe Ile Thr Glu  Ala Gly Asn
    1085                1090                1095

Leu Tyr  Tyr Phe Gly Gln Asp  Gly Tyr Met Val Thr  Gly Ala Gln
    1100                1105                1110

Asn Ile  Lys Gly Ser Asn Tyr  Tyr Phe Leu Ala Asn  Gly Ala Ala
    1115                1120                1125

Leu Arg  Asn Thr Val Tyr Thr  Asp Ala Gln Gly Gln  Asn His Tyr
    1130                1135                1140

Tyr Gly  Asn Asp Gly Lys Arg  Tyr Glu Asn Gly Tyr  Gln Gln Phe
    1145                1150                1155

Gly Asn  Asp Ser Trp Arg Tyr  Phe Lys Asn Gly Val  Met Ala Leu
    1160                1165                1170

Gly Leu  Thr Thr Val Asp Gly  His Val Gln Tyr Phe  Asp Lys Asp
    1175                1180                1185

Gly Val  Gln Ala Lys Asp Lys  Ile Ile Val Thr Arg  Asp Gly Lys
    1190                1195                1200

Val Arg  Tyr Phe Asp Gln His  Asn Gly Asn Ala Val  Thr Asn Thr
    1205                1210                1215

Phe Val  Ala Asp Lys Thr Gly  His Trp Tyr Tyr Leu  Gly Lys Asp
    1220                1225                1230

Gly Val  Ala Val Thr Gly Ala  Gln Thr Val Gly Lys  Gln His Leu
    1235                1240                1245

Tyr Phe  Glu Ala Asn Gly Gln  Gln Val Lys Gly Asp  Phe Val Thr
    1250                1255                1260

Ala Lys  Asp Gly Lys Leu Tyr  Phe Tyr Asp Val Asp  Ser Gly Asp
    1265                1270                1275

Met Trp  Thr Asn Thr Phe Ile  Glu Asp Lys Ala Gly  Asn Trp Phe
    1280                1285                1290

Tyr Leu  Gly Lys Asp Gly Ala  Ala Val Thr Gly Ala  Gln Thr Ile
    1295                1300                1305

Lys Gly  Gln Lys Leu Tyr Phe  Lys Ala Asn Gly Gln  Gln Val Lys
    1310                1315                1320

Gly Asp  Ile Val Lys Asp Ala  Asp Gly Lys Ile Arg  Tyr Tyr Asp
    1325                1330                1335

Ala Gln  Thr Gly Glu Gln Val  Phe Asn Lys Ser Val  Ser Val Asn
    1340                1345                1350

Gly Lys  Thr Tyr Tyr Phe Gly  Ser Asp Gly Thr Ala  Gln Thr Gln
    1355                1360                1365

Ala Asn  Pro Lys Gly Gln Thr  Phe Lys Asp Gly Ser  Gly Val Leu
    1370                1375                1380
```

```
Arg Phe Tyr Asn Leu Glu Gly Gln Tyr Val Ser Gly Ser Gly Trp
        1385                1390                1395

Tyr Glu Thr Ala Glu His Glu Trp Val Tyr Val Lys Ser Gly Lys
1400                1405                1410

Val Leu Thr Gly Ala Gln Thr Ile Gly Asn Gln Arg Val Tyr Phe
    1415                1420                1425

Lys Asp Asn Gly His Gln Val Lys Gly Gln Leu Val Thr Gly Asn
1430                1435                1440

Asp Gly Lys Leu Arg Tyr Tyr Asp Ala Asn Ser Gly Asp Gln Ala
    1445                1450                1455

Phe Asn Lys Ser Val Thr Val Asn Gly Lys Thr Tyr Tyr Phe Gly
1460                1465                1470

Ser Asp Gly Thr Ala Gln Thr Gln Ala Asn Pro Lys Gly Gln Thr
    1475                1480                1485

Phe Lys Asp Gly Ser Gly Val Leu Arg Phe Tyr Asn Leu Glu Gly
1490                1495                1500

Gln Tyr Val Ser Gly Ser Gly Trp Tyr Lys Asn Ala Gln Gly Gln
    1505                1510                1515

Trp Leu Tyr Val Lys Asp Gly Lys Val Leu Thr Gly Leu Gln Thr
1520                1525                1530

Val Gly Asn Gln Lys Val Tyr Phe Asp Lys Asn Gly Ile Gln Ala
    1535                1540                1545

Lys Gly Lys Ala Val Arg Thr Ser Asp Gly Lys Val Arg Tyr Phe
1550                1555                1560

Asp Glu Asn Ser Gly Ser Met Ile Thr Asn Gln Trp Lys Phe Val
    1565                1570                1575

Tyr Gly Gln Tyr Tyr Tyr Phe Gly Ser Asp Gly Ala Ala Val Tyr
1580                1585                1590

Arg Gly Trp Asn
1595

<210> SEQ ID NO 3
<211> LENGTH: 3039
<212> TYPE: DNA
<213> ORGANISM: Streptococcus downei
<220> FEATURE:
<221> NAME/KEY: CDS
<222> LOCATION: (1)..(3036)
<223> OTHER INFORMATION: variable region plus active core region of
      mutansucrase gene
<220> FEATURE:
<221> NAME/KEY: misc_feature
<222> LOCATION: (4)..(324)
<223> OTHER INFORMATION: variable region of mutansucrase gene
<220> FEATURE:
<221> NAME/KEY: active core region
<222> LOCATION: (325)..(3036)
<223> OTHER INFORMATION: active core region of mutansucrase gene
<220> FEATURE:
<221> NAME/KEY: mutation
<222> LOCATION: (3038)..(3038)
<223> OTHER INFORMATION: C to A
<220> FEATURE:
<221> NAME/KEY: mutation
<222> LOCATION: (1)..(3)
<223> OTHER INFORMATION: GAT to GGG

<400> SEQUENCE: 3 ggg act gaa act gtt agc gaa gac agc aac caa gca gtc ttg acg gct      48
Gly Thr Glu Thr Val Ser Glu Asp Ser Asn Gln Ala Val Leu Thr Ala
1               5                   10                  15 gac caa acg act acc aac caa gat act gag caa act tct gtt gca gcg      96
Asp Gln Thr Thr Thr Asn Gln Asp Thr Glu Gln Thr Ser Val Ala Ala
```

```
                20                  25                  30
aca gct aca tca gaa cag tct gct tca act gat gca gca aca gat caa      144
Thr Ala Thr Ser Glu Gln Ser Ala Ser Thr Asp Ala Ala Thr Asp Gln
             35                  40                  45 gca tca gca aca gat caa gca tca gca gca gag caa act caa gga aca      192
Ala Ser Ala Thr Asp Gln Ala Ser Ala Ala Glu Gln Thr Gln Gly Thr
 50                  55                  60 aca gct agc aca gac acg gca gct caa aca acc aca aat gct aat gaa      240
Thr Ala Ser Thr Asp Thr Ala Ala Gln Thr Thr Thr Asn Ala Asn Glu
 65                  70                  75                  80 gct aag tgg gtt ccg act gaa aat gag aac caa gtt ttt aca gat gag      288
Ala Lys Trp Val Pro Thr Glu Asn Glu Asn Gln Val Phe Thr Asp Glu
                 85                  90                  95 atg tta gca gaa gcc aag aat gtg gct act gct gaa tct aat tca att      336
Met Leu Ala Glu Ala Lys Asn Val Ala Thr Ala Glu Ser Asn Ser Ile
            100                 105                 110 cca tca gac ttg gct aaa atg tca aat gtt aag cag gtt gac ggt aaa      384
Pro Ser Asp Leu Ala Lys Met Ser Asn Val Lys Gln Val Asp Gly Lys
            115                 120                 125 tat tat tac tac gat caa gac ggc aac gtt aag aag aac ttt gct gtt      432
Tyr Tyr Tyr Tyr Asp Gln Asp Gly Asn Val Lys Lys Asn Phe Ala Val
            130                 135                 140 agc gtt ggt gag aag atc tat tac ttt gat gaa act ggc gct tac aaa      480
Ser Val Gly Glu Lys Ile Tyr Tyr Phe Asp Glu Thr Gly Ala Tyr Lys
145                 150                 155                 160 gac act agc aag gta gaa gcg gat aaa tca ggt tct gat atc agc aaa      528
Asp Thr Ser Lys Val Glu Ala Asp Lys Ser Gly Ser Asp Ile Ser Lys
                165                 170                 175 gaa gaa aca acc ttt gct gct aac aac cgt gct tac agt acc tca gct      576
Glu Glu Thr Thr Phe Ala Ala Asn Asn Arg Ala Tyr Ser Thr Ser Ala
            180                 185                 190 gaa aac ttt gaa gcc att gat aac tac ttg aca gct gac tca tgg tac      624
Glu Asn Phe Glu Ala Ile Asp Asn Tyr Leu Thr Ala Asp Ser Trp Tyr
            195                 200                 205 cgt cca aag tct atc ctc aag gat ggt aag act tgg aca gaa tca agc      672
Arg Pro Lys Ser Ile Leu Lys Asp Gly Lys Thr Trp Thr Glu Ser Ser
            210                 215                 220 aag gat gac ttc cgt ccg cta ttg atg gct tgg tgg cca gat acc gaa      720
Lys Asp Asp Phe Arg Pro Leu Leu Met Ala Trp Trp Pro Asp Thr Glu
225                 230                 235                 240 acc aaa cgc aac tat gtt aac tac atg aac aag gtt gtt ggt atc gat      768
Thr Lys Arg Asn Tyr Val Asn Tyr Met Asn Lys Val Val Gly Ile Asp
                245                 250                 255 aaa acc tat acc gct gaa aca agc cag gct gac ctg aca gca gca gct      816
Lys Thr Tyr Thr Ala Glu Thr Ser Gln Ala Asp Leu Thr Ala Ala Ala
            260                 265                 270 gaa ctg gtt caa gcc cgt atc gaa caa aag att aca act gaa caa aat      864
Glu Leu Val Gln Ala Arg Ile Glu Gln Lys Ile Thr Thr Glu Gln Asn
            275                 280                 285 acc aaa tgg ttg cgt gaa gct atc tca gct ttt gtt aaa act caa cca      912
Thr Lys Trp Leu Arg Glu Ala Ile Ser Ala Phe Val Lys Thr Gln Pro
            290                 295                 300 caa tgg aat ggt gaa agc gaa aag cca tac gat gac cac ttg caa aat      960
Gln Trp Asn Gly Glu Ser Glu Lys Pro Tyr Asp Asp His Leu Gln Asn
305                 310                 315                 320 ggt gcc ctc aag ttc gat aac caa tct gat ttg aca cca gat acg caa     1008
Gly Ala Leu Lys Phe Asp Asn Gln Ser Asp Leu Thr Pro Asp Thr Gln
            325                 330                 335 tcg aac tat cgt ttg ctc aat cgc aca cca act aac caa act ggt tcc     1056
Ser Asn Tyr Arg Leu Leu Asn Arg Thr Pro Thr Asn Gln Thr Gly Ser
```

-continued

```
                340                 345                 350
ctg gac tct cgt ttc acc tac aat gct aac gac ccg tta ggt ggt tat       1104
Leu Asp Ser Arg Phe Thr Tyr Asn Ala Asn Asp Pro Leu Gly Gly Tyr
        355                 360                 365 gag ttg ctt ctg gct aac gac gtg gat aac tct aat ccc atc gtt caa       1152
Glu Leu Leu Leu Ala Asn Asp Val Asp Asn Ser Asn Pro Ile Val Gln
370                 375                 380 gca gag caa ctc aac tgg ctg cat tac ctg ctc aac ttc ggt act atc       1200
Ala Glu Gln Leu Asn Trp Leu His Tyr Leu Leu Asn Phe Gly Thr Ile
385                 390                 395                 400 tat gct aaa gat gcg gat gct aac ttt gac tct atc cgt gtt gat gcg       1248
Tyr Ala Lys Asp Ala Asp Ala Asn Phe Asp Ser Ile Arg Val Asp Ala
                405                 410                 415 gta gat aat gtc gat gct gac ctt ctg caa atc tct agt gat tac ctt       1296
Val Asp Asn Val Asp Ala Asp Leu Leu Gln Ile Ser Ser Asp Tyr Leu
        420                 425                 430 aag gca gct tac ggt atc gat aaa aac aac aaa aat gct aat aac cac       1344
Lys Ala Ala Tyr Gly Ile Asp Lys Asn Asn Lys Asn Ala Asn Asn His
                435                 440                 445 gtt tct atc gta gaa gca tgg agc gac aac gat acc cct tat ctc cat       1392
Val Ser Ile Val Glu Ala Trp Ser Asp Asn Asp Thr Pro Tyr Leu His
450                 455                 460 gat gat ggc gac aac ctc atg aac atg gac aac aag ttc cgt ttg tct       1440
Asp Asp Gly Asp Asn Leu Met Asn Met Asp Asn Lys Phe Arg Leu Ser
465                 470                 475                 480 atg ctt tgg tct ttg gct aaa cca ttg gac aaa cgt tct ggc ttg aat       1488
Met Leu Trp Ser Leu Ala Lys Pro Leu Asp Lys Arg Ser Gly Leu Asn
                485                 490                 495 ccc ctc atc cac aac agt ctg gtt gac cgt gaa gtg gat gac cgt gaa       1536
Pro Leu Ile His Asn Ser Leu Val Asp Arg Glu Val Asp Asp Arg Glu
        500                 505                 510 gtt gaa acc gtt cca agt tac agc ttt gcc cgt gct cac gat agc gaa       1584
Val Glu Thr Val Pro Ser Tyr Ser Phe Ala Arg Ala His Asp Ser Glu
                515                 520                 525 gta caa gac ctg att cgt gac atc atc aag gct gaa att aat cca aat       1632
Val Gln Asp Leu Ile Arg Asp Ile Ile Lys Ala Glu Ile Asn Pro Asn
530                 535                 540 gca ttt ggt tat tca ttt act caa gac gaa atc gac caa gcc ttc aag       1680
Ala Phe Gly Tyr Ser Phe Thr Gln Asp Glu Ile Asp Gln Ala Phe Lys
545                 550                 555                 560 att tac aac gaa gac ctc aag aag acc gat aag aaa tac act cac tac       1728
Ile Tyr Asn Glu Asp Leu Lys Lys Thr Asp Lys Lys Tyr Thr His Tyr
                565                 570                 575 aat gtg ccg ctt tct tat acc ttg ctt ctg act aac aag ggt tcg att       1776
Asn Val Pro Leu Ser Tyr Thr Leu Leu Leu Thr Asn Lys Gly Ser Ile
        580                 585                 590 cct cgc gtc tat tat gga gat atg ttc acc gat gat ggt caa tac atg       1824
Pro Arg Val Tyr Tyr Gly Asp Met Phe Thr Asp Asp Gly Gln Tyr Met
                595                 600                 605 gcc aac aag act gtg aac tac gat gct atc gaa tct ctg ctg aaa gcc       1872
Ala Asn Lys Thr Val Asn Tyr Asp Ala Ile Glu Ser Leu Leu Lys Ala
610                 615                 620 cgt atg aag tac gtt gct ggt ggt caa gct atg caa aat tac caa atc       1920
Arg Met Lys Tyr Val Ala Gly Gly Gln Ala Met Gln Asn Tyr Gln Ile
625                 630                 635                 640 ggt aat ggc gaa atc ttg act tct gtc cgt tat ggt aag ggt gcc ctt       1968
Gly Asn Gly Glu Ile Leu Thr Ser Val Arg Tyr Gly Lys Gly Ala Leu
                645                 650                 655 aaa caa agc gat aag ggt gat gcg aca act cgt acg tca ggt gtc ggc       2016
Lys Gln Ser Asp Lys Gly Asp Ala Thr Thr Arg Thr Ser Gly Val Gly
```

```
                    660                665                670
gtt gtt atg gga aac caa ccc aac ttt agc ttg gat gga aag gtt gta    2064
Val Val Met Gly Asn Gln Pro Asn Phe Ser Leu Asp Gly Lys Val Val
            675                680                685 gcc ctc aac atg ggt gct gcc cac gct aac caa gaa tac cgt gct ctt    2112
Ala Leu Asn Met Gly Ala Ala His Ala Asn Gln Glu Tyr Arg Ala Leu
        690                695                700 atg gta tca act aaa gac ggt gtt gca acc tat gct aca gat gct gat    2160
Met Val Ser Thr Lys Asp Gly Val Ala Thr Tyr Ala Thr Asp Ala Asp
705                710                715                720 gct agc aag gct ggt ctg gtt aag cgc aca gat gaa aat ggt tac ctc    2208
Ala Ser Lys Ala Gly Leu Val Lys Arg Thr Asp Glu Asn Gly Tyr Leu
            725                730                735 tac ttc ttg aac gac gat ctc aag ggg gtt gct aac cct cag gtt tct    2256
Tyr Phe Leu Asn Asp Asp Leu Lys Gly Val Ala Asn Pro Gln Val Ser
        740                745                750 ggt ttc ctt caa gtc tgg gta cca gtg gga gca gca gat gac caa gat    2304
Gly Phe Leu Gln Val Trp Val Pro Val Gly Ala Ala Asp Asp Gln Asp
755                760                765 att cgt gta gca gct agc gat aca gca agt acc gat gga aaa tca ctc    2352
Ile Arg Val Ala Ala Ser Asp Thr Ala Ser Thr Asp Gly Lys Ser Leu
            770                775                780 cat caa gat gct gcc atg gac tct cgc gtc atg ttt gaa ggt ttc tct    2400
His Gln Asp Ala Ala Met Asp Ser Arg Val Met Phe Glu Gly Phe Ser
785                790                795                800 aac ttc caa tct ttt gcg aca aaa gaa gaa gag tat acc aat gtt gtt    2448
Asn Phe Gln Ser Phe Ala Thr Lys Glu Glu Glu Tyr Thr Asn Val Val
            805                810                815 att gct aac aat gtt gat aaa ttt gtt tca tgg gga atc act gac ttt    2496
Ile Ala Asn Asn Val Asp Lys Phe Val Ser Trp Gly Ile Thr Asp Phe
        820                825                830 gaa atg gct cct cag tat gtc tca tct act gac ggt cag ttc ctt gat    2544
Glu Met Ala Pro Gln Tyr Val Ser Ser Thr Asp Gly Gln Phe Leu Asp
835                840                845 tct gtc att caa aat ggt tat gcc ttt acc gac cgt tat gac ttg ggt    2592
Ser Val Ile Gln Asn Gly Tyr Ala Phe Thr Asp Arg Tyr Asp Leu Gly
850                855                860 atg tct aaa gca aac aag tat ggt aca gcc gac caa ttg gtt aag gct    2640
Met Ser Lys Ala Asn Lys Tyr Gly Thr Ala Asp Gln Leu Val Lys Ala
865                870                875                880 atc aag gct ctc cat gct aaa ggc ctg aag gtt atg gca gac tgg gtt    2688
Ile Lys Ala Leu His Ala Lys Gly Leu Lys Val Met Ala Asp Trp Val
            885                890                895 cca gac caa atg tac acc ttc cct aaa caa gaa gtg gtc act gtt act    2736
Pro Asp Gln Met Tyr Thr Phe Pro Lys Gln Glu Val Val Thr Val Thr
        900                905                910 cgg aca gat aag ttt ggc aaa cca atc gca gga agc caa att aat cac    2784
Arg Thr Asp Lys Phe Gly Lys Pro Ile Ala Gly Ser Gln Ile Asn His
915                920                925 agt ctc tac gta aca gat aca aag agc tct ggt gat gac tat caa gct    2832
Ser Leu Tyr Val Thr Asp Thr Lys Ser Ser Gly Asp Asp Tyr Gln Ala
        930                935                940 aaa tac ggc ggt gcc ttc ctt gac gaa tta aag gaa aaa tat cca gaa    2880
Lys Tyr Gly Gly Ala Phe Leu Asp Glu Leu Lys Glu Lys Tyr Pro Glu
945                950                955                960 ctc ttt acc aag aag caa atc tct acc ggc caa gcc ata gat cca tct    2928
Leu Phe Thr Lys Lys Gln Ile Ser Thr Gly Gln Ala Ile Asp Pro Ser
            965                970                975 gtt aag att aaa caa tgg tct gct aag tac ttc aac ggt agc aat atc    2976
Val Lys Ile Lys Gln Trp Ser Ala Lys Tyr Phe Asn Gly Ser Asn Ile
```

```
                         980             985             990
ctt ggc cgg ggt gcc gat tat gtc  ctc agc gac caa gca  agc aac aag   3024
Leu Gly Arg Gly Ala Asp Tyr Val  Leu Ser Asp Gln Ala  Ser Asn Lys
        995                 1000                 1005 tac ctc  aat gtt taa                                                3039
Tyr Leu  Asn Val
    1010

<210> SEQ ID NO 4
<211> LENGTH: 1012
<212> TYPE: PRT
<213> ORGANISM: Streptococcus downei
<220> FEATURE:
<221> NAME/KEY: misc_feature
<222> LOCATION: (4)..(324)
<223> OTHER INFORMATION: variable region of mutansucrase gene

<400> SEQUENCE: 4

Gly Thr Glu Thr Val Ser Glu Asp Ser Asn Gln Ala Val Leu Thr Ala
1               5                   10                  15

Asp Gln Thr Thr Thr Asn Gln Asp Thr Glu Gln Thr Ser Val Ala Ala
            20                  25                  30

Thr Ala Thr Ser Glu Gln Ser Ala Ser Thr Asp Ala Ala Thr Asp Gln
        35                  40                  45

Ala Ser Ala Thr Asp Gln Ala Ser Ala Ala Glu Gln Thr Gln Gly Thr
    50                  55                  60

Thr Ala Ser Thr Asp Thr Ala Ala Gln Thr Thr Thr Asn Ala Asn Glu
65                  70                  75                  80

Ala Lys Trp Val Pro Thr Glu Asn Glu Asn Gln Val Phe Thr Asp Glu
                85                  90                  95

Met Leu Ala Glu Ala Lys Asn Val Ala Thr Ala Glu Ser Asn Ser Ile
            100                 105                 110

Pro Ser Asp Leu Ala Lys Met Ser Asn Val Lys Gln Val Asp Gly Lys
        115                 120                 125

Tyr Tyr Tyr Tyr Asp Gln Asp Gly Asn Val Lys Lys Asn Phe Ala Val
    130                 135                 140

Ser Val Gly Glu Lys Ile Tyr Tyr Phe Asp Glu Thr Gly Ala Tyr Lys
145                 150                 155                 160

Asp Thr Ser Lys Val Glu Ala Asp Lys Ser Gly Ser Asp Ile Ser Lys
                165                 170                 175

Glu Glu Thr Thr Phe Ala Ala Asn Asn Arg Ala Tyr Ser Thr Ser Ala
            180                 185                 190

Glu Asn Phe Glu Ala Ile Asp Asn Tyr Leu Thr Ala Asp Ser Trp Tyr
        195                 200                 205

Arg Pro Lys Ser Ile Leu Lys Asp Gly Lys Thr Trp Thr Glu Ser Ser
    210                 215                 220

Lys Asp Asp Phe Arg Pro Leu Leu Met Ala Trp Trp Pro Asp Thr Glu
225                 230                 235                 240

Thr Lys Arg Asn Tyr Val Asn Tyr Met Asn Lys Val Val Gly Ile Asp
                245                 250                 255

Lys Thr Tyr Thr Ala Glu Thr Ser Gln Ala Asp Leu Thr Ala Ala Ala
            260                 265                 270

Glu Leu Val Gln Ala Arg Ile Glu Gln Lys Ile Thr Thr Glu Gln Asn
        275                 280                 285

Thr Lys Trp Leu Arg Glu Ala Ile Ser Ala Phe Val Lys Thr Gln Pro
    290                 295                 300

Gln Trp Asn Gly Glu Ser Glu Lys Pro Tyr Asp Asp His Leu Gln Asn
```

-continued

```
            305                 310                 315                 320
Gly Ala Leu Lys Phe Asp Asn Gln Ser Asp Leu Thr Pro Asp Thr Gln
                325                 330                 335
Ser Asn Tyr Arg Leu Leu Asn Arg Thr Pro Thr Asn Gln Thr Gly Ser
                340                 345                 350
Leu Asp Ser Arg Phe Thr Tyr Asn Ala Asn Asp Pro Leu Gly Gly Tyr
                355                 360                 365
Glu Leu Leu Ala Asn Asp Val Asp Asn Ser Asn Pro Ile Val Gln
            370                 375                 380
Ala Glu Gln Leu Asn Trp Leu His Tyr Leu Leu Asn Phe Gly Thr Ile
385                 390                 395                 400
Tyr Ala Lys Asp Ala Asp Ala Asn Phe Asp Ser Ile Arg Val Asp Ala
                405                 410                 415
Val Asp Asn Val Asp Ala Asp Leu Leu Gln Ile Ser Ser Asp Tyr Leu
                420                 425                 430
Lys Ala Ala Tyr Gly Ile Asp Lys Asn Asn Lys Asn Ala Asn Asn His
                435                 440                 445
Val Ser Ile Val Glu Ala Trp Ser Asp Asn Asp Thr Pro Tyr Leu His
            450                 455                 460
Asp Asp Gly Asp Asn Leu Met Asn Met Asp Asn Lys Phe Arg Leu Ser
465                 470                 475                 480
Met Leu Trp Ser Leu Ala Lys Pro Leu Asp Lys Arg Ser Gly Leu Asn
                485                 490                 495
Pro Leu Ile His Asn Ser Leu Val Asp Arg Glu Val Asp Asp Arg Glu
                500                 505                 510
Val Glu Thr Val Pro Ser Tyr Ser Phe Ala Arg Ala His Asp Ser Glu
                515                 520                 525
Val Gln Asp Leu Ile Arg Asp Ile Ile Lys Ala Glu Ile Asn Pro Asn
            530                 535                 540
Ala Phe Gly Tyr Ser Phe Thr Gln Asp Glu Ile Asp Gln Ala Phe Lys
545                 550                 555                 560
Ile Tyr Asn Glu Asp Leu Lys Lys Thr Asp Lys Lys Tyr Thr His Tyr
                565                 570                 575
Asn Val Pro Leu Ser Tyr Thr Leu Leu Leu Thr Asn Lys Gly Ser Ile
                580                 585                 590
Pro Arg Val Tyr Tyr Gly Asp Met Phe Thr Asp Asp Gly Gln Tyr Met
                595                 600                 605
Ala Asn Lys Thr Val Asn Tyr Asp Ala Ile Glu Ser Leu Leu Lys Ala
                610                 615                 620
Arg Met Lys Tyr Val Ala Gly Gln Ala Met Gln Asn Tyr Gln Ile
625                 630                 635                 640
Gly Asn Gly Glu Ile Leu Thr Ser Val Arg Tyr Gly Lys Gly Ala Leu
                645                 650                 655
Lys Gln Ser Asp Lys Gly Asp Ala Thr Arg Thr Ser Gly Val Gly
                660                 665                 670
Val Val Met Gly Asn Gln Pro Asn Phe Ser Leu Asp Gly Lys Val Val
                675                 680                 685
Ala Leu Asn Met Gly Ala Ala His Ala Asn Gln Glu Tyr Arg Ala Leu
                690                 695                 700
Met Val Ser Thr Lys Asp Gly Val Ala Thr Tyr Ala Thr Asp Ala Asp
705                 710                 715                 720
Ala Ser Lys Ala Gly Leu Val Lys Arg Thr Asp Glu Asn Gly Tyr Leu
                725                 730                 735
```

```
Tyr Phe Leu Asn Asp Asp Leu Lys Gly Val Ala Asn Pro Gln Val Ser
                740                 745                 750

Gly Phe Leu Gln Val Trp Val Pro Val Gly Ala Ala Asp Gln Asp
            755                 760                 765

Ile Arg Val Ala Ala Ser Asp Thr Ala Ser Thr Asp Gly Lys Ser Leu
770                 775                 780

His Gln Asp Ala Ala Met Asp Ser Arg Val Met Phe Glu Gly Phe Ser
785                 790                 795                 800

Asn Phe Gln Ser Phe Ala Thr Lys Glu Glu Tyr Thr Asn Val Val
                805                 810                 815

Ile Ala Asn Asn Val Asp Lys Phe Val Ser Trp Gly Ile Thr Asp Phe
                820                 825                 830

Glu Met Ala Pro Gln Tyr Val Ser Ser Thr Asp Gly Gln Phe Leu Asp
                835                 840                 845

Ser Val Ile Gln Asn Gly Tyr Ala Phe Thr Arg Tyr Asp Leu Gly
850                 855                 860

Met Ser Lys Ala Asn Lys Tyr Gly Thr Ala Asp Gln Leu Val Lys Ala
865                 870                 875                 880

Ile Lys Ala Leu His Ala Lys Gly Leu Lys Val Met Ala Asp Trp Val
                885                 890                 895

Pro Asp Gln Met Tyr Thr Phe Pro Lys Gln Glu Val Val Thr Val Thr
                900                 905                 910

Arg Thr Asp Lys Phe Gly Lys Pro Ile Ala Gly Ser Gln Ile Asn His
                915                 920                 925

Ser Leu Tyr Val Thr Asp Thr Lys Ser Ser Gly Asp Asp Tyr Gln Ala
                930                 935                 940

Lys Tyr Gly Gly Ala Phe Leu Asp Glu Leu Lys Glu Lys Tyr Pro Glu
945                 950                 955                 960

Leu Phe Thr Lys Lys Gln Ile Ser Thr Gly Gln Ala Ile Asp Pro Ser
                965                 970                 975

Val Lys Ile Lys Gln Trp Ser Ala Lys Tyr Phe Asn Gly Ser Asn Ile
                980                 985                 990

Leu Gly Arg Gly Ala Asp Tyr Val  Leu Ser Asp Gln Ala  Ser Asn Lys
                995                 1000                1005

Tyr Leu  Asn Val
    1010

<210> SEQ ID NO 5
<211> LENGTH: 24
<212> TYPE: DNA
<213> ORGANISM: Artificial Sequence
<220> FEATURE:
<223> OTHER INFORMATION: Forward Primer

<400> SEQUENCE: 5
agcttgcggc cccgggactg aaac                                          24

<210> SEQ ID NO 6
<211> LENGTH: 25
<212> TYPE: DNA
<213> ORGANISM: Artificial Sequence
<220> FEATURE:
<223> OTHER INFORMATION: Reverse Primer

<400> SEQUENCE: 6
gtggtggtgg aattcgagtt agttc                                         25

<210> SEQ ID NO 7
```

```
<211> LENGTH: 31
<212> TYPE: DNA
<213> ORGANISM: Artificial Sequence
<220> FEATURE:
<223> OTHER INFORMATION: Reverse Primer

<400> SEQUENCE: 7
agaaggaatt ctcatcttaa acattgaggt a                           31

<210> SEQ ID NO 8
<211> LENGTH: 25
<212> TYPE: DNA
<213> ORGANISM: Artificial Sequence
<220> FEATURE:
<223> OTHER INFORMATION: Poly-dT Primer

<400> SEQUENCE: 8
tttttttttt tttttttttt ttttt                                  25

<210> SEQ ID NO 9
<211> LENGTH: 21
<212> TYPE: DNA
<213> ORGANISM: Artificial Sequence
<220> FEATURE:
<223> OTHER INFORMATION: GtfIRT primer

<400> SEQUENCE: 9
ccgtgcttac agtacctcag c                                      21

<210> SEQ ID NO 10
<211> LENGTH: 23
<212> TYPE: DNA
<213> ORGANISM: Artificial Sequence
<220> FEATURE:
<223> OTHER INFORMATION: GtfIRT primer

<400> SEQUENCE: 10
ggtcgttagc attgtaggtg aaa                                    23

<210> SEQ ID NO 11
<211> LENGTH: 20
<212> TYPE: DNA
<213> ORGANISM: Artificial Sequence
<220> FEATURE:
<223> OTHER INFORMATION: Ubi3 primer

<400> SEQUENCE: 11
gtcaggccca attacgaaga                                        20

<210> SEQ ID NO 12
<211> LENGTH: 19
<212> TYPE: DNA
<213> ORGANISM: Artificial Sequence
<220> FEATURE:
<223> OTHER INFORMATION: Ubi3 primer

<400> SEQUENCE: 12
aagttccagc accgcactc                                         19
```